(12) United States Patent
Walter et al.

(10) Patent No.: US 11,211,151 B2
(45) Date of Patent: Dec. 28, 2021

(54) INTEGRATED WORKFLOW FOR PROCESSING TISSUE SAMPLES FROM BREAST BIOPSY PROCEDURES

(71) Applicant: Devicor Medical Products, Inc., Cincinnati, OH (US)

(72) Inventors: Adam Walter, Mason, OH (US); Elijah Kreider, Hamilton, OH (US); Bryan R. Keller, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 427 days.

(21) Appl. No.: 15/638,843

(22) Filed: Jun. 30, 2017

(65) Prior Publication Data

US 2018/0004918 A1    Jan. 4, 2018

Related U.S. Application Data

(60) Provisional application No. 62/406,480, filed on Oct. 11, 2016, provisional application No. 62/357,474, filed on Jul. 1, 2016.

(51) Int. Cl.
*A61B 10/02* (2006.01)
*G06T 7/00* (2017.01)
(Continued)

(52) U.S. Cl.
CPC ......... *G16H 10/40* (2018.01); *A61B 10/0041* (2013.01); *A61B 10/02* (2013.01);
(Continued)

(58) Field of Classification Search
CPC .... G16H 10/40; A61B 10/0041; A61B 10/02; B01L 3/545; G01N 35/00029; G01N 35/00732; G06T 7/0012
(Continued)

(56) References Cited

U.S. PATENT DOCUMENTS 5,526,822 A   6/1996   Burbank et al.
5,607,863 A   3/1997   Chandler
(Continued)

FOREIGN PATENT DOCUMENTS

JP   2008-128749 A   6/2008
WO   WO 2003/042788 A2   5/2003
(Continued)

OTHER PUBLICATIONS

Pantanowitz, L. et al. (2013) "Tracking in Anatomic Pathology." Arch Pathol Lab Med. 137:1798-1810. (Year: 2013).*
(Continued)

*Primary Examiner* — Matthew D Krcha
*Assistant Examiner* — Jacqueline Brazin
(74) *Attorney, Agent, or Firm* — Frost Brown Todd LLC

(57) ABSTRACT

A method of obtaining and analyzing at least one tissue sample includes forming, in a tissue container, first tracking data associated with the at least one tissue sample. Second tracking data is formed, in a transport container. The second tracking data is associated with the at least one tissue sample. The at least one tissue sample is placed in the tissue container. The first and second tracking data from the tissue container and the transport container are scanned with an electronic scanning system to ensure that the first and second tracking data are both associated with the removed tissue sample.

16 Claims, 35 Drawing Sheets

(51) Int. Cl.
*G01N 33/574* (2006.01)
*A61B 10/00* (2006.01)
*G16H 10/40* (2018.01)
*G01N 35/00* (2006.01)
*B01L 3/00* (2006.01)

(52) U.S. Cl.
CPC ........ *B01L 3/545* (2013.01); *G01N 35/00029* (2013.01); *G01N 35/00732* (2013.01); *G06T 7/0012* (2013.01); *A61B 10/0096* (2013.01); *B01L 2200/18* (2013.01); *B01L 2300/021* (2013.01); *G01N 33/57415* (2013.01); *G01N 2035/00752* (2013.01); *G01N 2035/00772* (2013.01); *G01N 2035/00782* (2013.01); *G09G 2340/12* (2013.01)

(58) Field of Classification Search
USPC .......................................................... 436/43
See application file for complete search history.

(56) References Cited

U.S. PATENT DOCUMENTS

| | | | |
|---|---|---|---|
| 5,928,164 | A | 7/1999 | Burbank et al. |
| 6,017,316 | A | 1/2000 | Ritchart et al. |
| 6,086,544 | A | 7/2000 | Hibner et al. |
| 6,162,187 | A | 12/2000 | Buzzard et al. |
| 6,203,756 | B1 * | 3/2001 | Lin .......................... A61L 2/186 422/28 |
| 6,403,035 | B1 * | 6/2002 | Caratsch ................ G01N 35/04 422/65 |
| 6,432,065 | B1 | 8/2002 | Burdorff et al. |
| 6,626,849 | B2 | 9/2003 | Huitema et al. |
| 6,752,768 | B2 | 6/2004 | Burdorff et al. |
| 7,442,171 | B2 | 10/2008 | Stephens et al. |
| 7,648,466 | B2 | 1/2010 | Stephens et al. |
| 7,715,523 | B2 | 5/2010 | Lafferty |
| 7,837,632 | B2 | 11/2010 | Stephens et al. |
| 7,854,706 | B2 | 12/2010 | Hibner |
| 7,854,707 | B2 | 12/2010 | Hibner et al. |
| 7,914,464 | B2 | 3/2011 | Burdorff et al. |
| 7,938,786 | B2 | 5/2011 | Ritchie et al. |
| 8,083,687 | B2 | 12/2011 | Parihar |
| 8,118,755 | B2 | 2/2012 | Hibner et al. |
| 8,177,728 | B2 | 5/2012 | Hibner et al. |
| 8,206,316 | B2 | 6/2012 | Hibner et al. |
| 8,235,913 | B2 | 8/2012 | Hibner et al. |
| 8,241,226 | B2 | 8/2012 | Hibner et al. |
| 8,251,916 | B2 | 8/2012 | Speeg et al. |
| 8,454,531 | B2 | 6/2013 | Speeg et al. |
| 8,485,987 | B2 | 7/2013 | Videbaek et al. |
| 8,503,602 | B2 | 8/2013 | Lafferty |
| 8,532,747 | B2 | 9/2013 | Nock et al. |
| 8,628,482 | B2 | 1/2014 | Leimbach et al. |
| 8,702,623 | B2 | 4/2014 | Parihar et al. |
| 8,764,680 | B2 | 7/2014 | Rhad et al. |
| 8,801,742 | B2 | 8/2014 | Rhad et al. |
| 8,802,034 | B2 | 8/2014 | Bartfeld et al. |
| 8,858,465 | B2 | 10/2014 | Fiebig |
| 8,938,285 | B2 | 1/2015 | Fiebig et al. |
| 8,951,207 | B2 | 2/2015 | Hibner |
| 8,956,306 | B2 | 2/2015 | Hibner |
| 9,056,317 | B2 | 6/2015 | Bartfeld et al. |
| 9,095,326 | B2 | 8/2015 | Ritchie et al. |
| 9,289,192 | B2 | 3/2016 | Stone |
| 9,307,756 | B2 | 4/2016 | Clement et al. |
| 9,326,755 | B2 | 5/2016 | Fiebig et al. |
| 9,345,457 | B2 | 5/2016 | Speeg et al. |
| 9,389,153 | B2 | 7/2016 | Newby et al. |
| 9,409,164 | B2 | 8/2016 | Tawfik et al. |
| 9,486,186 | B2 | 11/2016 | Fiebig et al. |
| 9,724,076 | B2 | 8/2017 | Fiebig et al. |
| 9,834,810 | B2 | 12/2017 | Knapp, Jr. et al. |
| 9,877,706 | B2 | 1/2018 | Speeg et al. |
| 9,955,955 | B2 | 5/2018 | Fiebig et al. |
| 9,999,406 | B2 | 6/2018 | Hibner |
| 10,092,905 | B2 | 10/2018 | Fleming et al. |
| 2004/0215103 | A1 * | 10/2004 | Mueller, Jr. ........ A61B 10/0041 600/564 |
| 2006/0074345 | A1 | 4/2006 | Hibner |
| 2009/0131821 | A1 | 5/2009 | Speeg et al. |
| 2010/0152610 | A1 | 6/2010 | Parihar et al. |
| 2010/0160819 | A1 | 6/2010 | Parihar et al. |
| 2010/0160824 | A1 * | 6/2010 | Parihar ............... A61B 10/0096 600/567 |
| 2010/0167334 | A1 * | 7/2010 | Williamson, IV ..... G16H 10/40 435/29 |
| 2013/0324882 | A1 | 12/2013 | Mescher |
| 2014/0039343 | A1 | 2/2014 | Mescher et al. |
| 2015/0176055 | A1 * | 6/2015 | Knapp, Jr. .......... A61B 10/0096 435/6.1 |
| 2016/0183928 | A1 | 6/2016 | Speeg et al. |
| 2018/0000463 | A1 | 1/2018 | Keller |

FOREIGN PATENT DOCUMENTS

| | | |
|---|---|---|
| WO | WO 2007/014741 A2 | 2/2007 |
| WO | WO 2010/151761 A2 | 12/2010 |
| WO | WO 2011/144982 A1 | 11/2011 |
| WO | WO 2013/192606 A1 | 12/2013 |
| WO | WO 2013/192607 A1 | 12/2013 |
| WO | WO 2014/151603 A1 | 9/2014 |
| WO | WO 2015/042107 A1 | 3/2015 |

OTHER PUBLICATIONS

Hahn, M., et al., "Vacuum-Assisted Breast Biopsy with Mammotome®," Devicor Medical Germany GmbH, published in Germany by Springer Medizin Verlag, 2013, 130 pgs.
Rolls, G., "101 Steps To Better Histology," Lecia Biosystems, 2016, Lecia Biosystems Melbourne Pty. Ltd., Melbourne, Australia, 140 pgs.
Rolls, G., "An Introduction to Tissue Processing," Lecia Biosystems, 2016, Lecia Biosystems Melbourne Pty. Ltd., Melbourne, Australia, 57 pgs.
Leica Microsystems, "Total Histology Solutions: Leica Microsystems' Complete Histology Product Range," Sep. 2010, 28 pgs.
International Search Report and Written Opinion dated Nov. 17, 2017 for Application No. PCT/US2017/040277, 12 pgs.
International Search Report and Written Opinion dated Jan. 9, 2018 for Application No. PCT/US2017/040273, 20 pgs.
U.S. Appl. No. 62/357.474, filed Jul. 1, 2016.
U.S. Appl. No. 62/406.480, filed Oct. 11, 2016.
European Communication dated Feb. 8, 2019 for Application No. 17740199.9, 3 pages.
European Communication dated Dec. 6, 2019 for Application No. 17740199.9, 4 pages.

* cited by examiner

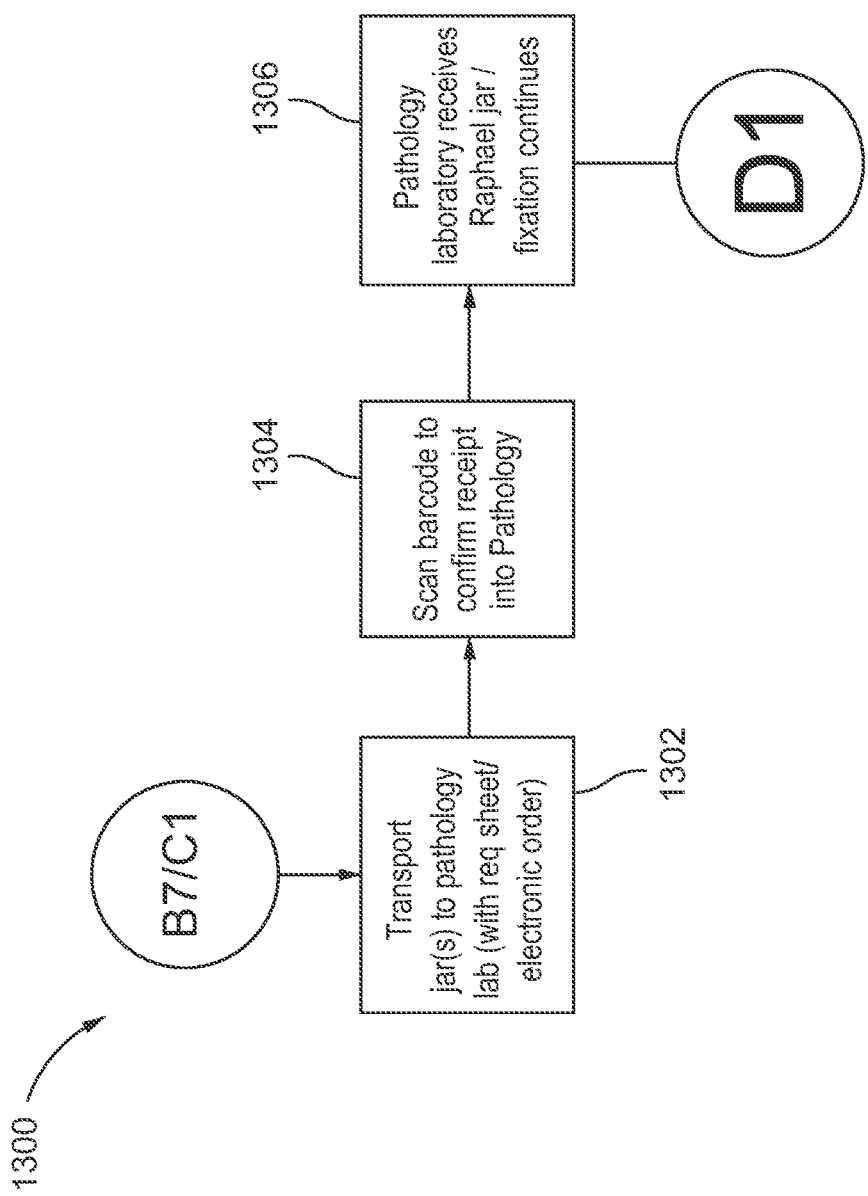

Legend:
 PURPLE COLOR SHOWN IN THIS DRAWING ONLY

INTEGRATED WORKFLOW FOR PROCESSING TISSUE SAMPLES FROM BREAST BIOPSY PROCEDURES

PRIORITY

The present application claims priority to U.S. Provisional Patent Application No. 62/357,474, entitled "Biopsy Sample Container," filed on Jul. 1, 2016; and U.S. Provisional Patent Application No. 62/406,480, entitled "Integrated Workflow for Processing Tissue Samples from Breast Biopsy Procedures," filed on Oct. 11, 2016, the disclosures of which are hereby incorporated by reference herein in their entirety.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological analysis).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

The state of the art for breast biopsy is vacuum-assisted breast biopsy. A current textbook in this area is "Vacuum-Assisted Breast Biopsy with Mammotome®" available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Biopsy devices may be used under ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following briefly describes ultrasound image guided biopsy procedures, stereotactic guided biopsy procedures and MRI guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator may create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using a medically acceptable way to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure may proceed with the acquisition of stereotactic image pairs. Stereotactic image pairs are acquired by orienting the x-ray source at various complementary angular positions relative to the x-ray receptor (e.g., +15° and −15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue, which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using a medically acceptable way to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "Mill Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454, 531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764, 680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015; U.S. Pat. No. 9,095,326, entitled "Biopsy System with Vacuum Control Module," issued Aug. 4, 2015 and U.S. Pat. No. 9,326, 755, entitled "Biopsy Device Tissue Sample Holder with Bulk Chamber and Pathology Chamber," issued May 3, 2016. The disclosure of each of the above-cited U.S. Patents is incorporated by reference herein.

Additional exemplary biopsy devices and biopsy system components are disclosed in U.S. Pub. No. 2006/0074345, entitled "Biopsy Apparatus and Method," published Apr. 6, 2006 and now abandoned; U.S. Pub. No. 2008/0214955, entitled "Presentation of Biopsy Sample by Biopsy Device," published Sep. 4, 2008; U.S. Pub. No. 2009/0131821, entitled "Graphical User Interface For Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; U.S. Pub. No. 2013/0144188, entitled "Biopsy Device With Slide-In Probe," published Jun. 6, 2013; and U.S. Pub. No. 2013/0324882, entitled "Control for Biopsy Device," published Dec. 5, 2013. The disclosure of each of the above-cited U.S. Patent Application Publications is incorporated by reference herein.

U.S. Pub. No. 2014/0275999, entitled "Biopsy device" published Sep. 18, 2014, and U.S. Pub. No. 2016/0183928, entitled "Biopsy Device," published Jun. 30, 2016, both describe some aspect of a biopsy device including a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

Leica Biosystems is a global leader in workflow solutions and automation, providing anatomic pathology labs and researchers a comprehensive product range for each step in the pathology process from sample preparation and staining to imaging and reporting. Leica Biosystems has published on their website informational booklets that are accessible via download and that contain information on various aspects of the pathology process. These booklets include, but are not limited to: "An Introduction to Tissue Processing" by Geoffrey Rolls, "101 Steps to Better Histology," and "Total Histology Solutions," all of which are available via www.leicabiosystems.com.

At several steps during tissue processing using conventional techniques and instruments, it may be necessary to manually manipulate the tissue. This manual manipulation may take time and introduce the possibility of human error causing mistakes during the processing of tissue. Any and all mistakes during the processing of tissue may make the pathological examination of the tissue much more problematic to achieve the desired goal of having an accurate diagnosis. Thus, it is understood that a desired goal of modern tissue processing is the reduction of the requirement that tissue be manually manipulated.

International Pat. Pub. No. WO 2013/192606, entitled "Biopsy Tissue Sample Transport Device and Method of Using Thereof," published on Dec. 27, 2013, describes a biopsy tissue sample transport device and method of using the same including a tissue storage assembly having a sample container, having a holding structure to hold a tissue sample, the holding structure having a sample access opening formed in a sidewall; a housing that receives the tissue storage assembly, the housing comprising an assembly insertion opening through which the tissue storage assembly is inserted into the housing; a sealing member configured to engage and substantially seal the sample access opening of the holding structure of the sample container of the tissue storage assembly; and a lid to engage and substantially seal the assembly insertion opening of the housing.

International Pat. Pub. No. WO 2013/192607, entitled "Tissue Sample Container and Methods," published on Dec. 27, 2013, describes a tissue sample container including a base having a plurality of sample holding sections, which are configured to receive a plurality of tissue samples in a given orientation and are demarcated by section walls; and a lid configured to sealingly engage the base. The sample holding sections are sized and shaped to correspond to a specific tissue sample size and shape such that the base in cooperation with the section walls, maintain the given orientation and identity of the tissue samples within respective sample holding sections.

International Pat. Pub. No. WO 2014/151603, entitled "Biopsy Device," published on Sep. 25, 2014, describes a biopsy device that includes a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

U.S. Pat. No. 7,715,523, entitled "System and Apparatus for Rapid Stereotactic Breast Biopsy Analysis," issued on May 11, 2010, and U.S. Pat. No. 8,503,602, entitled "System and Apparatus for Rapid Stereotactic Breast Biopsy Analysis," issued on Aug. 6, 2013, both describe a stereotactic breast biopsy apparatus and system that may comprise an x-ray source, a digital imaging receptor, and a biopsy specimen cassette, wherein the x-ray source is provided with a means for displacing the beam axis of the x-ray source from a working biopsy corridor beam axis to permit an unobstructed illumination of the biopsy specimen and thereby produce biopsy x-ray images directly in the procedure room for immediate analysis. Some examples of the benefits may be, but are not limited to, a more rapid analysis of biopsy specimen digital images, post-processing image capability, and decreased procedure time and diminution of patient bleeding complications and needle discomfort.

U.S. Pat. No. 8,485,987, entitled "Tissue Handling System with Reduced Operator Exposure," issued Jul. 16, 2016, describes a tissue handling system includes a biopsy device having an invasive unit with tissue-receiving and tissue-severing components being capable of harvesting and bringing at least one tissue sample to a point outside the body of a patient. The tissue handling system further includes a tissue collecting device adapted to be brought in detachable operative engagement with the tissue-receiving components of the biopsy device to remove the at least one tissue sample. Additionally, the tissue handling device comprises a tissue storage container configured to receive the at least one tissue sample, the entire tissue collecting device, or the part of the collecting device that contains the at least one tissue sample. The tissue storage container further is configured to receive a volume of preserving agent. The tissue handling system also comprises a vessel including the preserving agent adapted to be gas-tightly mated or coupled to the tissue storage container.

U.S. Pat. No. 8,802,034, entitled "Tissue Container for Molecular and Histology Diagnostics Incorporating a Breakable Membrane," issued on Aug. 12, 2014, describes a container for storing a biological sample for molecular diagnostic testing and/or histological testing. The container includes a first chamber for receiving a sample holder therein, a second chamber, and a closure for enclosing the container. A breakable membrane, such as a pierce-able foil, extends within the container and separates the two chambers. When the breakable membrane is broken, fluid can pass between the first and second chambers. The membrane may be broken through an activator on the closure, such as a depressible member or a rotatable carrier, causing the sample holder to break through the membrane.

U.S. Pat. No. 9,056,317, entitled "Tissue Container for Molecular and Histology Diagnostics Incorporating a Breakable Membrane," issued on Jun. 16, 2016 describes a container for storing a biological sample for molecular diagnostic testing and/or histological testing. The container includes a first chamber for receiving a sample holder therein, a second chamber, and a closure for enclosing the container. A breakable membrane, such as a pierce able foil, extends within the container and separates the two chambers. When the breakable membrane is broken, fluid can pass between the first and second chambers. The membrane may be broken through an activator on the closure, such as a depressible member or a rotatable carrier, causing the sample holder to break through the membrane.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 9H depicts a flow chart showing an exemplary process for transporting and tracking tissue samples acquired from the processes of FIGS. 9A-9G;

Figure 1:
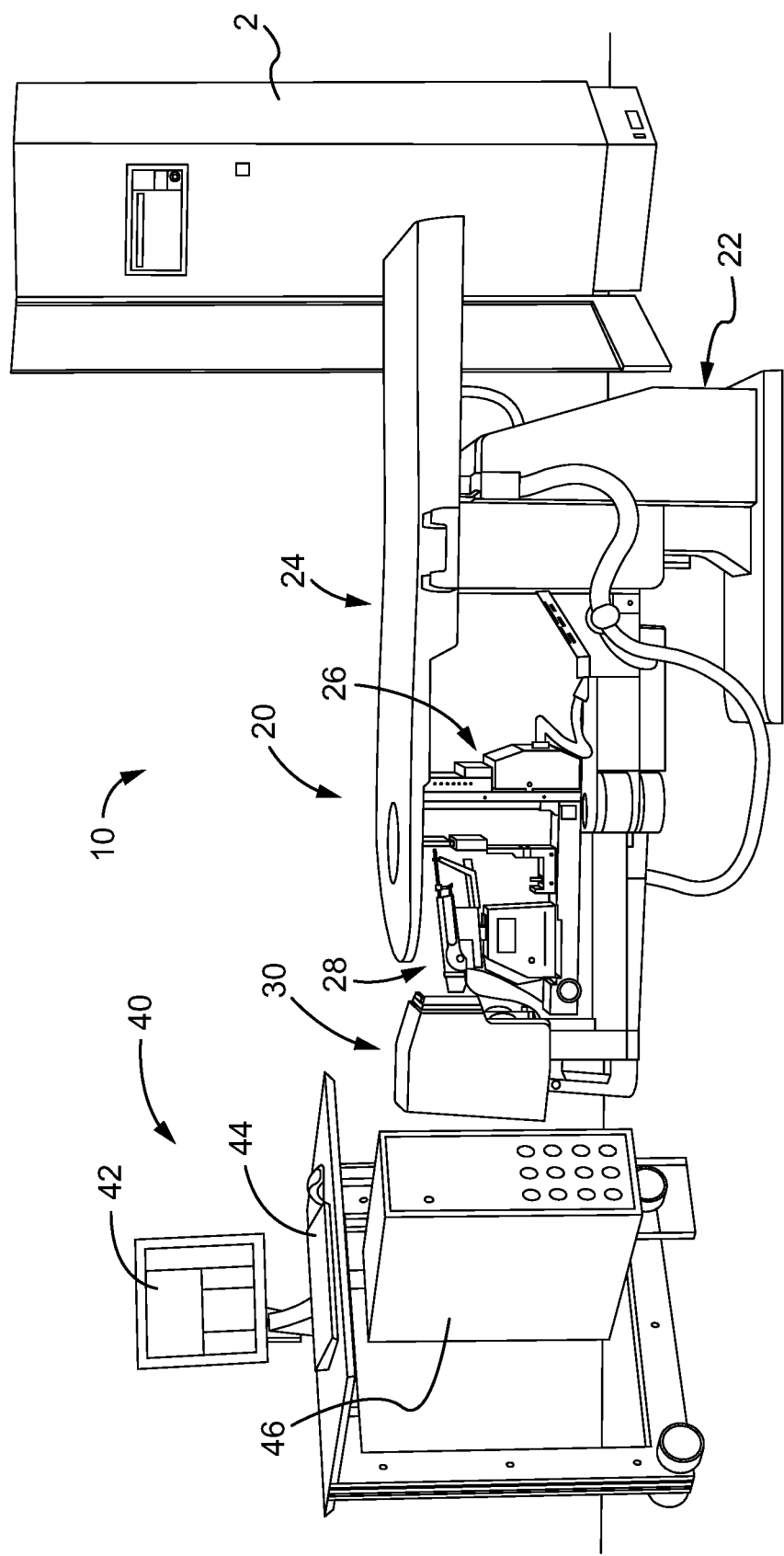
FIG. 1 depicts a perspective view of an exemplary biopsy suite.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Biopsy devices may be used to collect tissue samples in a variety of ways. For example, in some instances tissue samples are collected into a single tissue basket such that all tissue samples collected during a given biopsy procedure are deposited into the single tissue sample basket. In some other instances, tissue samples are collected into a tissue sample holder having separate compartments for each collected tissue sample. Such a multi-compartment tissue sample holder may additionally include trays or strips that individually hold each tissue sample separately from the other tissue samples. Such trays or strips may be removable or otherwise separable from the tissue sample holder at the conclusion of a biopsy procedure.

Regardless of the structure in which the tissue samples are stored, tissue samples may be collected under the guidance of various imaging modalities such as ultrasound, stereotactic x-ray, MRI, PEM/BSGI, and/or other imaging modalities.

In some instances, challenges may be encountered when transporting tissue samples through various diagnostic steps after the tissue samples have been collected. For example, in some procedures where tissue samples collected in a single sample basket, such tissue samples may be preliminarily laid out on gauze or a tray. In the case of separated tissue sample collection, trays or strips may be removed from the tissue sample holder and examined. Regardless, a specimen radiograph can then be performed in either the procedure room or at a remote location. Tissue samples may additionally be grouped and/or dyed at this stage. Once preliminary analysis has been completed, the tissue samples may then be loaded into a transport container or other container and then transported to a remote pathology lab.

One consequence of the procedure described above is that tracking of individual tissue samples may be challenging. However, it may nevertheless desirable to track individual tissue samples throughout the biopsy sampling and subsequent diagnostic procedures, including radiology and pathology. In some instances, such tracking may be desirable to enhance the ability to obtain specific analysis of tissue samples identified by the operator collecting biopsy samples. In addition, or in the alternative, such tracking may be desirable to avoid or otherwise prevent operator error during the entire biopsy sample collection and analysis process, including gaps or anomalies in the chain of custody of tissue samples.

Various systems and techniques are described herein that may be used to enhance the tracking of tissue samples as the tissue samples progress through the biopsy sample collection and analysis process, including radiology and pathology. In addition to providing a more robust chain of custody for tissue samples, the systems and techniques described herein may provide efficiencies that minimize the cold ischemic time of tissue samples, which may ultimately yield more trustworthy diagnoses. Although numerous features and configurations are described herein, it should be understood that various modifications may be made as will be apparent to those of ordinary skill in the art in view of the teachings herein.

I. Exemplary Biopsy Suite

FIG. 1 shows an exemplary stereotactic, also known as "X-Ray" biopsy suite (10). Suite (10) comprises a support assembly (20), a control module (40), and an X-ray generator (2). Support assembly (20) is connected to control module (40) and X-ray generator (2) via cables (not shown). Generally, and as will be described in greater detail below, support assembly (20) is operable to support a patient and immobilize the patient's breast to fix the breast relative to a fixed three-dimensional Cartesian coordinate system. With the patient's breast immobilized, support assembly (20) may be used to provide a plurality of radiographs using X-rays generated by X-ray generator (2). Control module (40) may then be used by an operator to analyze the radiographs. Specific locations of interest within the patient's breast may then be identified and their specific Cartesian coordinates stored using control module (40). Support assembly (20) may then be used to assist an operator with targeting the locations of interest with an attached biopsy device to extract tissue samples.

Some merely exemplary biopsy devices that may be used with suite (10) are disclosed in U.S. Pat. No. 7,854,707, entitled "Tissue Sample Revolver Drum Biopsy Device," issued Dec. 21, 2010; U.S. Pat. No. 8,083,687, entitled "Tissue Biopsy Device with Rotatably Liked Thumbwheel and Tissue Sample Holder," issued Dec. 27, 2011; and U.S. Pat. No. 8,241,226, entitled "Biopsy Device with Rotatable Tissue Sample Holder," issued Aug. 14, 2012, the disclosure of which is incorporated by reference herein. Alternatively, suite (10) may be used with any other biopsy devices, including but not limited to any of the biopsy devices disclosed in any of the various references that are incorporated by reference herein.

Control module (40) comprises a display screen (42), a user input apparatus (44), and a data processing and storage unit (46). By way of example only, display screen (42) may comprise a conventional computer monitor; user input apparatus (44) may comprise a conventional keyboard and mouse; and data processing and storage unit (46) may comprise a conventional computer that is modified to include software operable to execute the processes described herein. As will be described in greater detail below, control module (40) is configured to obtain and store radiographic images, execute various image processing algorithms, and display radiographic images based on user input for analysis. Although control module (40) is shown as having a particular configuration, it should be understood that control module may be configured in any suitable way as will be apparent to those of ordinary skill in the art in view of the teachings herein.

Support assembly (20) of the present example includes a base assembly (22) supporting a patient table (24), a breast compression assembly (26), a biopsy device guide assembly (28), and an x-ray tube assembly (30). Generally, base assembly (22) is adjustable to position table (24), breast compression assembly (26), biopsy device guide assembly (28), and x-ray tube assembly (30) relative to each other. For instance, in some examples, a patient is positioned in a prone position on table (24). Table (24) is configured such that one or more of a patient's breasts may extend downwardly though table (24) such that fixation of one or more breasts can be achieved using breast compression assembly (26). Once secured therein, the patient remains substantially stationary while biopsy device guide assembly (28) and x-ray tube assembly (30) are positioned relative to a patient.

In some examples, a stereoscopic imaging procedure is performed by pivoting x-ray tube assembly (30) into different stereotactic positions. Generally, this can involve pivoting x-ray tube assembly (30) into a first position at +15° (or some other angle) and then a second position at −15° (or some other angle) relative to its initial positon. Radiographs can be taken at each position and then control module (40) may triangulate specific regions of interest using triangulation. Regions of interest may then be targeted by a breast biopsy device under the guidance of biopsy device guide assembly (28). It should be understood that specific angular values provided herein are merely illustrative and in other examples numerous other angular values may be used. Moreover, while the various devices, configurations, features and methods are described herein in connection with a stereotactic biopsy suite (10), such devices, configurations, features and methods may be readily used in connection with other alternative biopsy suites. By way of example only, suitable biopsy suites may include ultrasound suites, MRI suites, and any other suitable kind of biopsy suite as will be apparent to those of ordinary skill in the art in view of the teachings herein.

II. Exemplary Biopsy System

Figure 2:
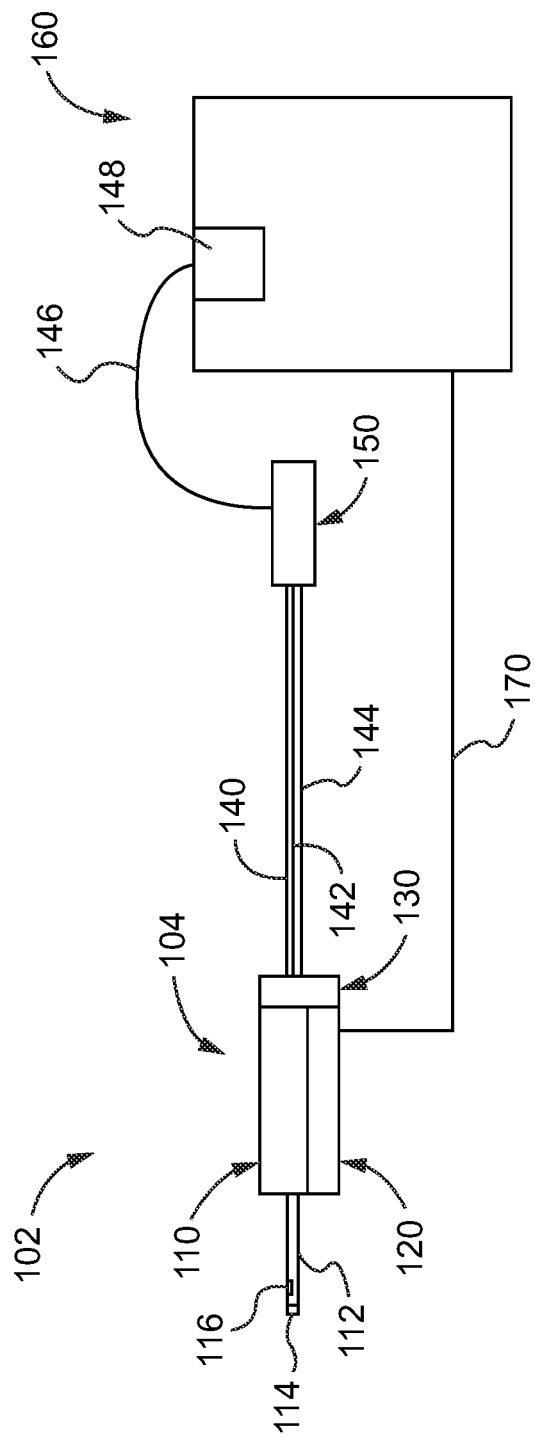
FIG. 2 depicts a schematic view of an exemplary biopsy system that is usable with the biopsy suite of FIG. 1.

FIG. 2 shows an exemplary biopsy system (102) that may be used within suite (10) under the guidance of biopsy device guide assembly (28) described above. Biopsy system (102) of the present example comprises a biopsy device (104), and a vacuum control module (160). Guide assembly (28) is configured and operable to provide structural support to biopsy device (104) and to guide biopsy device (104) in relation to the patient, in accordance with known structures and techniques.

Biopsy device (104) of this example comprises a probe (110) and a holster (120). A needle (112) extends distally from probe (110), and is insertable into a patient's tissue to obtain tissue samples. These tissue samples are then deposited in a tissue sample holder (130) at the proximal end of probe (110), as will be described in greater detail below. Biopsy device (104) of the present example is configured to mount to a table or fixture (e.g., guide assembly (28)), and be used under stereotactic guidance such as with suite (10) described above. Of course, biopsy device (104) may instead be used under ultrasound guidance, MRI guidance, PEM guidance, BSGI guidance, or otherwise. It should also be understood that biopsy device (104) may be sized and configured such that biopsy device (104) may be operated by a single hand of a user. In some settings, the user may capture a plurality of tissue samples with a single insertion of needle (112) into the patient's breast. Such tissue samples may be pneumatically deposited in tissue sample holder (130), and later retrieved from tissue sample holder (130) for analysis. Various exemplary components, features, configurations, and operabilities of biopsy device (104) will be described in greater detail below; while other suitable components, features, configurations, and operabilities will be apparent to those of ordinary skill in the art in view of the teachings herein.

In some examples, holster (120) includes gears or other mechanical transmission features that are configured to engage corresponding features of probe (110) and thereby communicate mechanical motion to probe (110). Although not shown, it should be understood that needle (112) includes a hollow cylindrical cutter extending into probe (110). This cutter is rotated in translated through a tissue sampling sequence via mechanical energy supplied by holster (120). In the tissue sampling sequence, tissue samples are acquired as cutter is driven past lateral aperture (116) on the exterior of needle (112). Such tissue samples are then communicated through probe (110) to tissue sample holder (130). In some examples, gears or other mechanical transmission features may additionally be configured to rotate needle (112). By way of example only, such a needle rotation mechanism may be constructed in accordance with the teachings of U.S. Pub. No. 2008/0214955, the disclosure of which is incorporated by reference herein; and/or U.S. Pub. No. 2010/0160819, the disclosure of which is incorporated by reference herein.

Holster (120) of the present example includes motors (not shown) to drive the gears to thereby rotate and translate cutter (112). Motors may additionally be used to actuate various features of tissue sample holder (130) as will be described in greater detail below. All motors referred to herein are contained within holster (120) in the present example and receive power from vacuum control module (160) via cable (170). In addition, data may be communicated between vacuum control module (160) and holster (120) via cable (170). In some other versions, one or more motors are powered by one or more batteries located within holster (120) and/or probe (110). It should also be understood that one motor, two motors, three motors, or more motors and/or other components (e.g., pneumatic features) may be used to provide the motion needed in order to acquire a tissue sample. Other suitable components and configurations will be apparent to those of ordinary skill in the art in view of the teachings herein.

As shown in FIG. 2, vacuum control module (160) is coupled with probe (110) via a valve assembly (150) and tubes (140, 142, 144, 146). Vacuum control module (160) is operable to selectively provide vacuum, saline, atmospheric air, and venting to probe (110). By way of example only, the internal components of the valve assembly of the present example may be configured and arranged as described in U.S. Pub. No. 2013/0218047, entitled "Biopsy Device Valve Assembly," published Aug. 22, 2013, the disclosure of which is incorporated by reference herein.

Needle (112) of the present example comprises a cannula having a tissue piercing tip (114), and a lateral aperture (116) located proximal to tip. By way of example only, tip (114) may be configured in accordance with any of the teachings in U.S. Pat. No. 8,801,742, entitled "Needle Assembly and Blade Assembly for Biopsy Device," issued Aug. 12, 2014, the disclosure of which is incorporated by reference herein; and/or U.S. Pub. No. 2013/0150751, entitled "Biopsy Device with Slide-In Probe," published Jun. 13, 2013, the disclosure of which is incorporated by reference herein. Other suitable configurations that may be used for tip (114) will be apparent to those of ordinary skill in the art in view of the teachings herein. Lateral aperture (116) is sized to receive prolapsed tissue during operation of device (104). Although not shown, it should be understood that a hollow tubular cutter having a sharp distal edge is located within needle (112). As described above, the cutter is operable to rotate and translate relative to needle (112) and past lateral aperture (116) to sever a tissue sample from tissue protruding through lateral aperture (116).

Although not shown, it should be understood that tissue sample holder (130) of the present example provides a plurality of discrete chambers that are configured to receive tissue samples that are severed by the cutter disposed within needle (112). In particular, and as will be described in greater detail below, tissue sample holder (130) includes tissue receiving trays (330) that are removably engaged with at least a portion of tissue sample holder (130). Various components within tissue sample holder (130) may be configured to rotate or otherwise move to sequentially position trays (330) into communication with the cutter disposed within needle (112). This positioning of trays (330) permits each tray (330) to separately receive a single tissue sample as tissue samples are collected by the cutter disposed within needle (112). An example of such a tissue sample holder (130) is disclosed in U.S. Pat. No. 9,345,457, entitled "Presentation of Biopsy Sample by Biopsy Device," issued May 24, 2016; and U.S. Pub. No. 2014/0275999, entitled "Biopsy Device," published on Sep. 18, 2014, the disclosures of which are incorporated by reference herein. Of course, as with any other component described herein, any other suitable configurations may be used.

Figure 3:
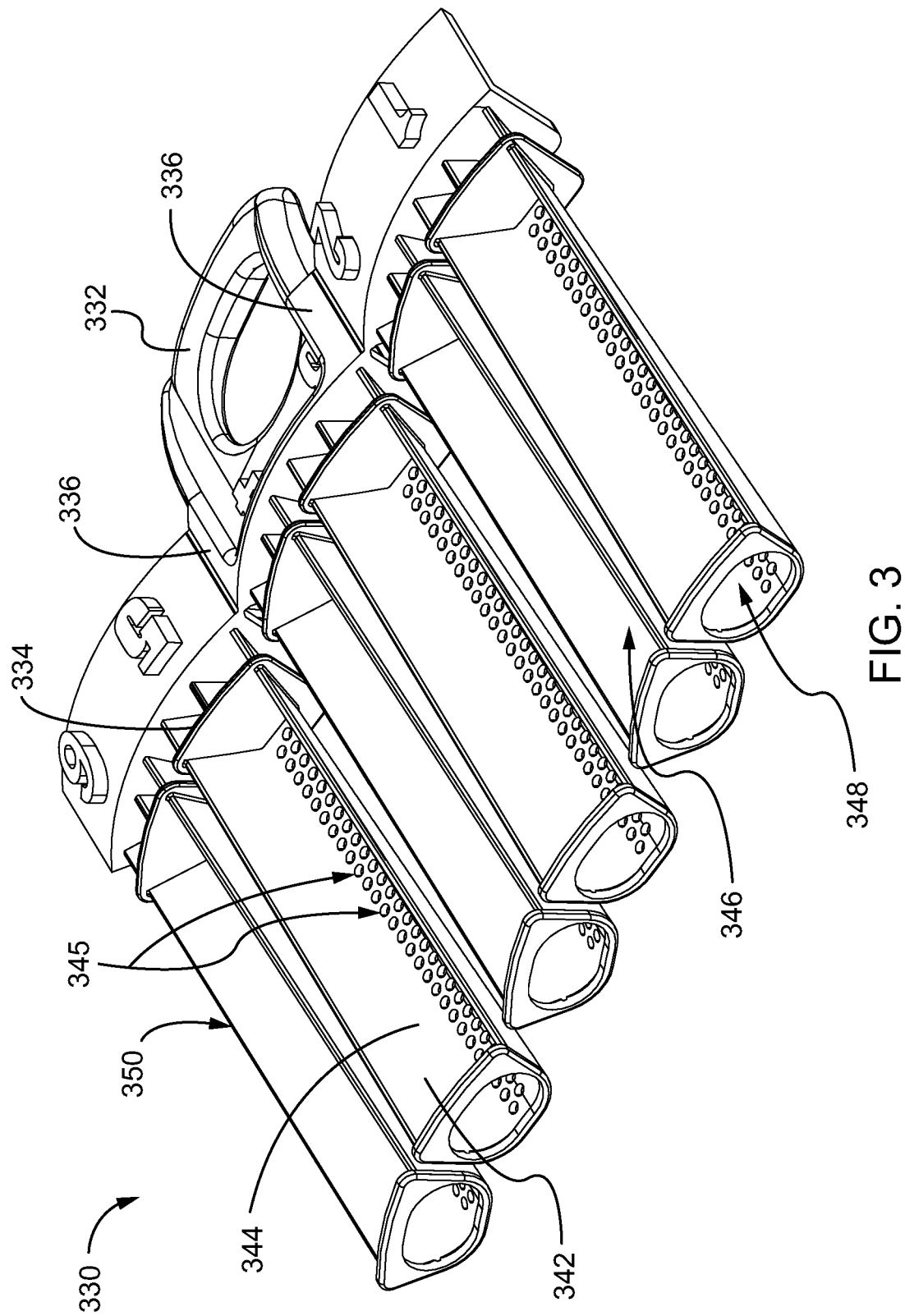
FIG. 3 depicts a perspective view of a tissue sample tray that is usable with a tissue sample holder of the biopsy system of FIG. 2.

FIG. 3 shows an exemplary tissue receiving tray (330). Tissue receiving tray (330) of this example includes a grip (332), a proximal wall (334), and a plurality of strips (350) extending distally from proximal wall (334). Strips (350) are sized and configured for insertion into associated passages (not shown) of tissue sample holder (130). Each strip (350) includes a pair of sidewalls (342) and a floor (344). Each pair of sidewalls (342) and floor (344) together define a corresponding tissue sample chamber (346). An opening (348) is provided at the distal end of each tissue sample chamber (346). Each floor (344) includes a plurality of openings (345) that provide fluid communication between tissue sample chamber (346) of strip (350) and the portion of tissue sample holder (130) associated with strip (360). Thus, vacuum, atmospheric air, etc. that is communicated to tissue sample holder (130) (e.g., via tubes (140, 142, 144)) is further communicated to the cutter disposed in needle (112) via openings (345) and tissue sample chamber (346).

Trays (330) further include living hinges (336) that facilitate flattening of trays (330). In particular, living hinges (336) provide sufficient flexibility to enable trays (330) to form an arcuate configuration for insertion into tissue sample holder (160); while also enabling trays (330) to form a generally flat configuration such as after trays (330) are removed from tissue sample holder (310) for inspection of tissue samples in trays (330), as will be described in greater detail below. By way of example only, trays (330) may be configured in accordance with any of the teachings in U.S. Pub. No. 2014/0275999, entitled "Biopsy Device," published Sep. 18, 2014, the disclosure of which is incorporated by reference herein. Of course, as with any other component described herein, any other suitable configurations may be used.

III. Exemplary Tissue Imaging System

Figure 4:
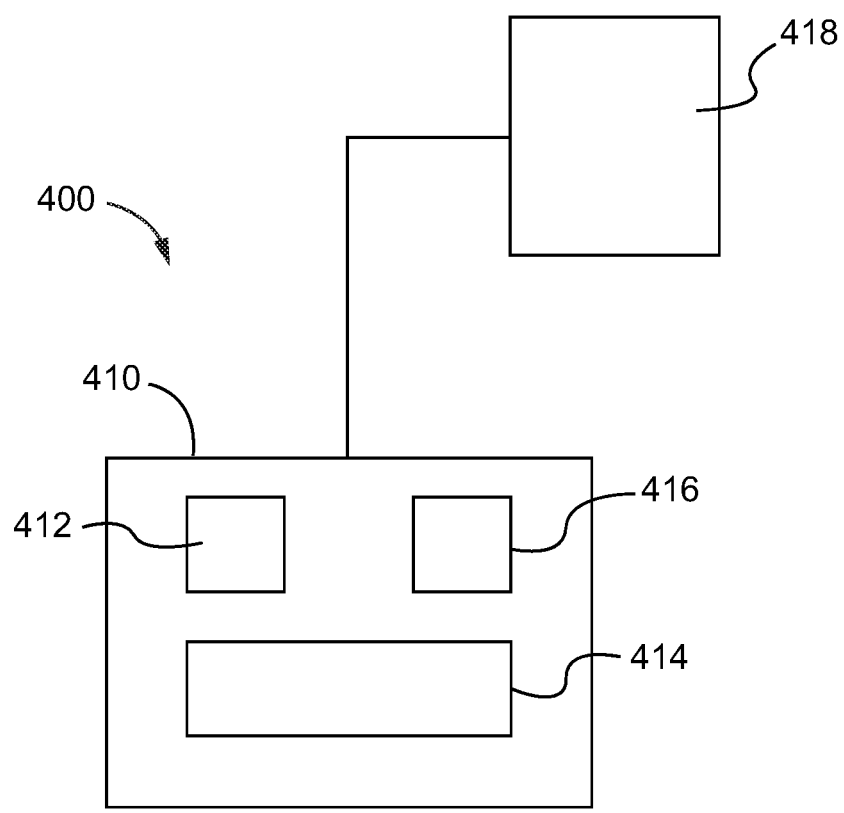
FIG. 4 depicts a schematic view of a tissue imaging system that is usable with the tissue sample tray of FIG. 3.

After a tissue sample is collected by biopsy device (102), it may be desirable to image such tissue samples, such as to detect the presence of calcifications or other anomalies. FIG. 4 shows an exemplary imaging system (400) that may be used to provide imaging of such tissue samples. It should be understood that, in some instances, imaging system (400) may be located within suite (10). Furthermore, in some versions, imaging system (400) may be integrated into control module (40) and/or otherwise integrated into one or more of the components shown in FIG. 1.

Imaging system (400) of the present example comprises an imaging control module (410) coupled with a display (418). Imaging control module (410) includes a slot (414) configured to receive one or more tissue trays (330) after collection of tissue samples by biopsy device (102). As will be described in greater detail below, slot (414) of the present example is configured to receive at least one tray (330) after it has been deposited in a tissue sample container (500). Alternatively, in some versions, slot (414) directly insertingly receives one or more tissue sample trays (330) and at least a portion of tissue sample holder (130). In some other versions, slot (414) includes a drawer or tray that slides into and out of imaging control module (410), such that tissue sample trays (330) may be placed in the drawer or on the tray, with the drawer or tray then retracting back into imaging control module (410) for imaging the tissue samples.

Imaging control module (410) of the present example further comprises an imaging device (412) and a data processor (416). Imaging device (412) may be configured to perform x-ray imaging of the tissue samples using an x-ray source (not shown) to emit x-rays, and an x-ray imaging sensor (not shown). In particular, the x-ray source may be mounted to an upper portion of the imaging control module (410) and may radiate electromagnetic radiation in the form of x-rays towards tissue samples in tissue sample receiving trays (330) loaded into slot (414). The radiation may then pass through the tissue sample at an angle approximately perpendicular to the longitudinal axis of each tissue sample contained in the tissue sample trays (330). The radiation may then strike the x-ray imaging sensor mounted to the bottom of imaging control module (410), thereby providing an image of each tissue sample. Although the present example may use two-dimensional x-ray imaging, it should be understood that various imaging methods may be used such as tomosynthesis, magnetic resonance, Positron Emission Tomography, etc. Moreover, the source and the x-ray imaging sensor may be oriented at different angles relative to each tissue sample contained in tissue sample trays (330) (e.g., source and x-ray imaging sensor mounted to opposing sidewalls of imaging control module (410)).

Images obtained using imaging device (412) may be processed by data processor (416) and communicated to display (418). Display (418) then provides an image of the tissue samples to a user for analyzing. In some versions, imaging system (400) may comprise a CoreVision® Specimen Radiography System manufactured by Faxitron Bioptics, LLC of Tucson, Ariz. Alternatively, any other imaging system (400) may be used as will be apparent to those of ordinary skill in the art in view of the teachings herein.

IV. Exemplary Tissue Sample Tray Container

Figure 5:
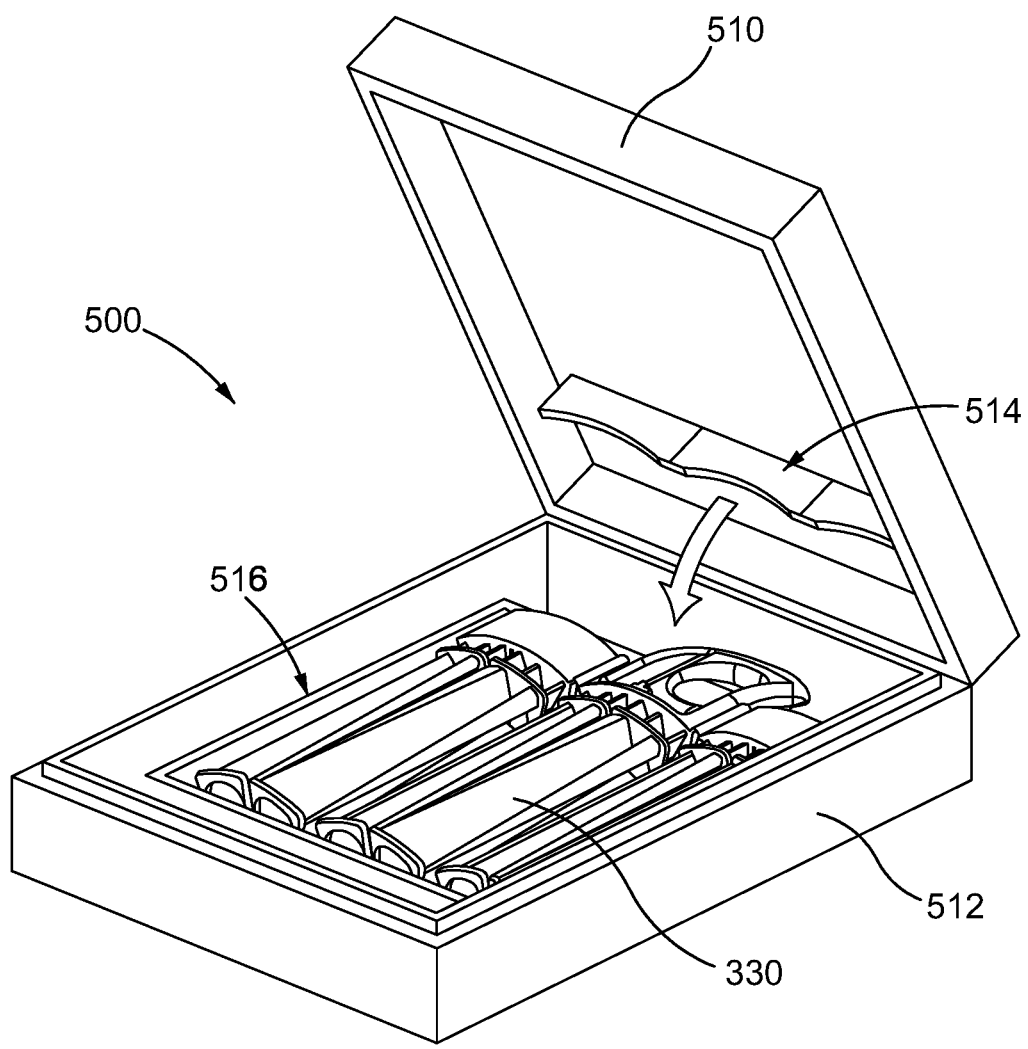
FIG. 5 depicts a perspective view of an exemplary tissue container that is usable with the tissue sample tray of FIG. 3 and the tissue imaging system of FIG. 4.
Figure 6:
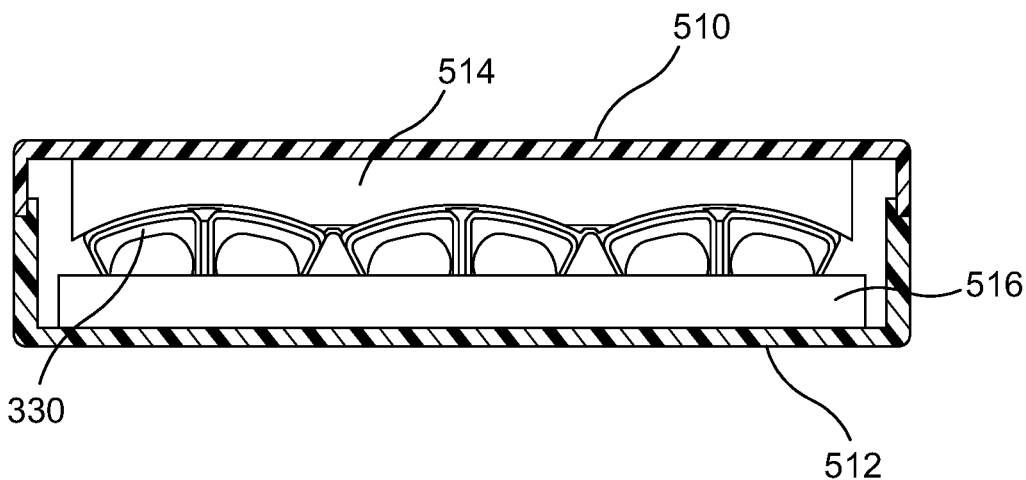
FIG. 6 depicts a side cross-sectional view of the tissue container of FIG. 5.

FIGS. 5 and 6 show an exemplary tissue sample tray container (500). Container (500) comprises a base (512) and a cover (510). In the present example, base (512) includes a guide (516) with walls extending from the bottom surface of base (512) that are sized to receive tray (330) in a flattened configuration. Cover (510) is coupled with base (512) such that cover (510) is pivotable relative to base (512). Accordingly, cover (510) may be opened relative to base (512) to allow base (512) to receive tray (330), as shown in FIG. 5; and cover (510) may then be closed relative to base (512) to enclose tray (330) within container (500) for imaging, as shown in FIG. 6. Alternatively, cover (510) may be decoupled from base (512) to insert tray (330) within base (512).

Cover (510) comprises a tab (514) extending within container (500). As shown in

FIG. 6, tab (514) is configured to engage tray (330) when cover (510) is closed relative to base (512). Tab (514) thereby maintains tray (330) in the flattened configuration for imaging. In the present example, the end portion of tab (514) has an arcuate configuration to align with strips (350) of tissue sample tray (330). Cover (510) and/or base (512) may further be made of a transparent material to allow for optical imaging or other optical observation of the tissue samples within tray (330).

Tray (330) is inserted within container (500) when container (500) is in the open configuration, as shown in FIG. 5. Tray (330) is in the flattened configuration and is maintained within guide (516) of base (512). Cover (510) is then pivoted relative to base (512) to close container (500), as shown in FIG. 6. Tab (514) thereby engages tray (330) to maintain tray (330) in the flattened configuration. Container (500) may be inserted within slot (414) of imaging system (400) such that the tissue samples within tray (330) may be imaged by imaging system (500).

Figure 7:
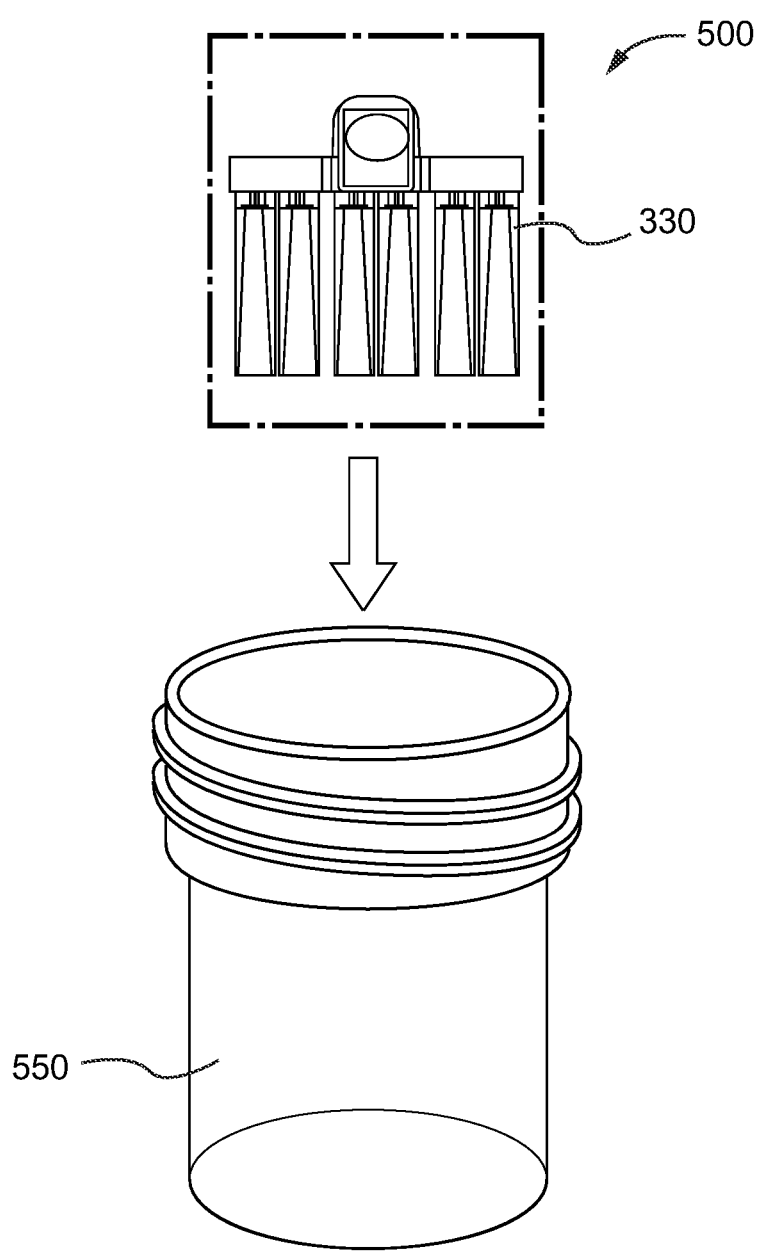
FIG. 7 depicts a perspective view of a sample jar that is configured to receive the tissue container of FIG. 5.

Container (500) of the present example is also configured for insertion into a transport container (550). In particular, as can be seen in FIG. 7 container (500) can be inserted into transport container (550) after imaging for storage or transport purposes, as will be described in greater detail below. Although not shown, it should be understood that in some examples container (500) may include ports or other openings that permit a fixative (e.g., formalin, saline, and/or etc.) to pass through container (500) to soak the tissue samples contained therein in the fixative. Although not shown it, transport container (550) also comprises a lid that is configured to close and seal transport container (550).

Although uses described herein contemplate imaging tissue samples prior to insertion into transport container (550), it should be understood that in some exemplary uses transport container (550) itself may be inserted into imaging system (400) after container (500) is inserted into transport container (550). Alternatively, container (500) may be filled with the fixative before container (500) is closed and placed in slot (414) of imaging system (400).

V. Exemplary Tissue Tracking System

Figure 8:
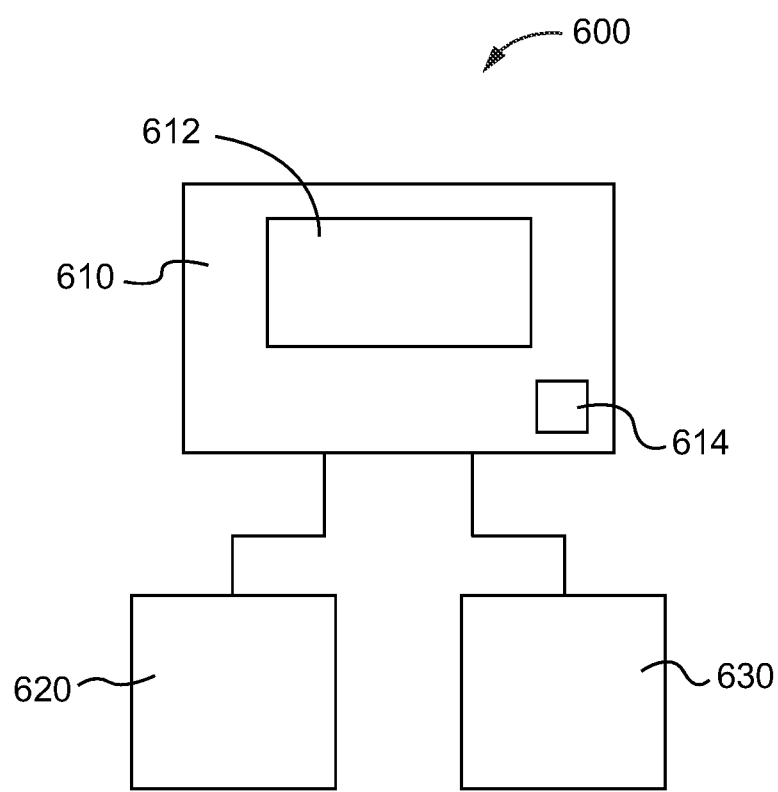
FIG. 8 depicts a block schematic view of an exemplary tissue tracking system for use with the tissue container of FIG. 5 and the sample jar of FIG. 7.

FIG. 8 shows an exemplary tissue tracking system (600) for use with the various components described above. Various suitable uses of tissue tracking system (600) will be described in greater detail below. Tissue tracking system (600) comprises a control unit (610), a printer (620), and a scanner (630). Generally, tissue tracking system (600) is usable in connection with tissue sample tray (330), container (500), and transport container (550) to assist an operator in tracking tissue samples as they move through the biopsy procedure and subsequent pathological analysis procedures. As will be described in greater detail below, control unit (610) is in communication with printer (620) and scanner (630) to print and catalogue various labels for use on any one or more of tissue sample tray (330), container (500), and transport container (550).

Control unit (610) comprises a user interface feature (612) and various processing components contained within control unit (610). User interface feature (612) of the present example comprises a screen that is configured to display various graphics such as a graphical user interface to access patent information and/or other data. By way of example only, user interface feature (612) can additionally include touch screen functionality to facilitate user interaction with control unit (610). In other examples, control unit (610) may include other user input features in addition or in lieu of touch screen functionality. Suitable user input features can include keyboards, and/or pointing devices such as mice, trackballs, and/or touchpads.

Control unit (610) further comprises a network interface feature (614). Network interface feature (614) is configured to permit control unit (610) to interface with a local area network. In some instances, network interface feature (614) may interface directly or indirectly with a laboratory information system such as a picture archiving and communication system (PACS) to facilitate uploading and downloading various patient files and/or data. Network interface feature (614) of the present example is configured to communicate with local area networks though a wired connection. However, it should be understood that in other examples network interface feature (614) can include wireless communication features in addition to or in lieu of wired connections to permit such communication with local area networks.

Printer (620) of the present example is remote from control unit (610) but is in communication with control unit (610) via wireless or wired connectivity. Although printer (620) is shown as being remote from control unit (610), it should be understood that in some examples printer (620) can be fully integrated into control unit (610). Printer (62) of the present example is generally configured to print labels based on instructions provided by control unit (610). In some instances, printing can be performed directly on labels comprising a pressure sensitive adhesive for attachment to trays (330), container (500), and/or transport container (550). Such labels can also be resistant to formalin, bio-products, or other moisture.

Scanner (630) of the present example is also remote from control unit (610) but in communication with control unit (610) via wireless or wired connectivity. Although scanner (630) is shown as being remote from control unit (610), it should be understood that in some examples scanner (630) can be fully integrated into control unit (610). Scanner (630) of the present example is generally configured to scan labels and communicate information contained on such labels to control unit (610). In some instances, this may include scanning bar codes or other optical machine-readable representations of data. Accordingly, it should be understood that scanner (630) can include various scanning devices such as lasers, CCDs, or the like. In addition, or in the alternative, scanner (630) may include certain radio frequency identification (RFID) reading and writing features. In such examples, labels printed by printer (620) can include RFID chips that may be written and read by scanner (630). While it is contemplated that such RFID technology may be used in conjunction with printer (620), it should be understood that in other examples printer (620) may be eliminated entirely and only RFID chips may be used for tracking in accordance with the uses and methods described below. While optical tags and RFID tags are provided as examples herein, other suitable kinds of tags, etc., that may be used will be apparent to those of ordinary skill in the art in view of the teachings herein. Regardless of the particular configuration of scanner (630) it should be understood that once information is scanned, said information can be transmitted electronically to remote locations or a laboratory information system via scanner (630) itself or control unit (610).

VI. Exemplary Method of Acquiring, Tracking, and Analyzing Tissue Samples

FIGS. 9A-9L show a flowchart of an exemplary integrated workflow that may be performed utilizing biopsy suite (10), biopsy system (102), tissue sample tray (330), tissue imaging system (400), tissue container (500), and tissue tracking system (600) described above. It should be understood that while biopsy suite (10), biopsy system (102), tissue sample tray (330), tissue imaging system (400), tissue container (500), and tissue tracking system (600) are used in the current example, any other suitable components and systems, etc., may be used in lieu of any of the above mentioned components and systems as would be apparent to one having ordinary skill in the art in view of the teachings herein.

Figure 9A:
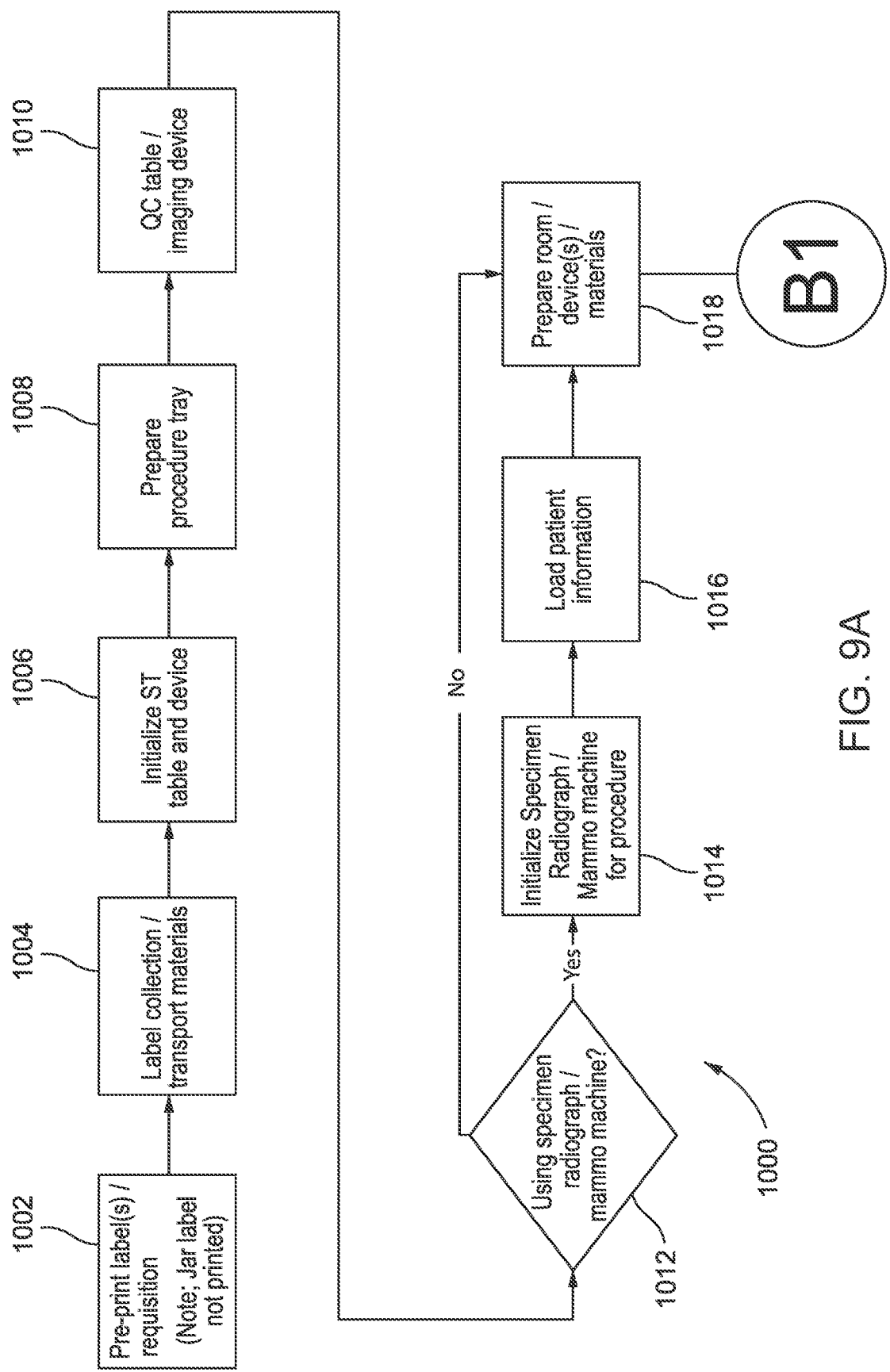
FIG. 9A depicts a flow chart showing an exemplary process for preparing the stereographic biopsy suite of FIG. 1.

FIG. 9A shows a method of preparing exemplary biopsy suite (10); FIGS. 9B-9G show a method of acquiring tissue samples from a patient and storing the tissue samples; FIG. 9H shows a method of transporting stored tissue samples from biopsy suite (10) to a pathology lab; FIGS. 9I-9J show a method of processing transported tissue samples at the pathology lab; FIG. 9K shows a method of performing a diagnosis after tissue samples have been processed at the pathology lab; and FIG. 9L shows methods for storing tissue samples and delivering results of diagnosis to a patient. Each of these processes will be described in greater detail below.

A. Exemplary Method of Preparing a Biopsy Suite

As noted above, FIG. 9A shows an exemplary preparation process (1000) for biopsy suite (10). As shown in block (1002), process (1000) starts with preprinting of label(s) and requisition of tissue containers (500) that will be used to store tissue sample trays (330) holding tissue samples. Label(s) may be printed with printer (620) and contain any suitable information as would be apparent to one having ordinary skill in the art in view of the teachings herein (e.g., patient reference, user reference, time/date stamp, etc.). Information for the labels may be entered via interface feature (612) of tissue tracking system (600) and/or may be electronically transmitted from other components within the system. Preprinting label(s) for tissue containers (500) may initiate a robust chain of custody of stored tissue samples. It should be understood that, in some instances, labels for jars (550) that store tissue containers (500) are not necessarily printed out at this point.

Next, as shown in block (1004), the preprinted labels generated in block (1002) are applied to tissue containers (500). To the extent that pre-applying the labels to containers (500) adds time to the process at this stage, the cost in time may be worth the immediate correlation between containers (500) and the biopsy procedure that will soon begin. In other words, applying labels to containers (500) before the biopsy procedure may reduce the risk of error (e.g., failure to apply labels to containers (500), mis-applying labels to containers (500), etc.) that might otherwise be greater in settings where labels are applied to containers (500) after a biopsy procedure.

Next, as shown in blocks (1006, 1008, 1010), various equipment in suite (10) is prepared for use. In particular, as shown in block (1006), support assembly (20) and biopsy system (102) are initialized. Such initialization may include powering on support assembly (20) and biopsy system (102), allowing support assembly (20) and biopsy system (102) to perform self-diagnostics, calibrating support assembly (20) and biopsy system (102), and/or various other kinds of initialization tasks as will be apparent to those of ordinary skill in the art in view of the teachings herein.

As shown in block (1008), a procedure tray is also prepared. It should be understood that such a procedure tray may be configured to support containers (500) and/or various other components that may be used during the subsequent procedure. These various other components can include useful items such as needles, syringes, anesthetic, sterile drapes, etc.

As shown in outline form in block (1010), control module (40) and x-ray generator (2) may then be initialized and/or otherwise prepared for use. Such initialization may include powering on control module (40) and x-ray generator (2), allowing control module (40) and x-ray generator (2) to perform self-diagnostics, calibrating control module (40) and x-ray generator (2), and/or various other kinds of initialization tasks as will be apparent to those of ordinary skill in the art in view of the teachings herein.

As shown in block (1012), the next step in process (1000) will depend on whether imaging system (400) will being used. If imaging system (400) will not be used, then process (1000) advances to the step shown in block (1018), which will be described in greater detail below. However, if imaging system (400) will be used, then the next step would be to initialize imaging system (400) as shown in block (1014). Such initialization may include powering on imaging system (400), allowing imaging system (400) to perform self-diagnostics, calibrating imaging system (400), and/or various other kinds of initialization tasks as will be apparent to those of ordinary skill in the art in view of the teachings herein.

With imaging system (400) initialized, and as shown in block (1016), the operator then loads patient information into control module (40), imaging system (400) and/or tissue tracking system (600). In addition, or in the alternative, the loading of information represented by block (1016) may include pulling up the patient's information on control module (40), imaging system (400), and/or tissue tracking system (600). It should also be understood that, in some versions, control module (400), imaging system (400), and tissue tracking system (600) may all be in communication with each other and/or integrated into a single unit. The single unit is envisioned to be able to communicate with the hospital or clinic medical records system. At present, these medical record systems include, but are not limited to HIS for Hospital Information System, EMR for Electronic Medical System, RIS for Radiology Information System and LIS for Laboratory Information System. Thus, patient related information and/or other information may be communicated electronically between control module (400), imaging system (400), and tissue tracking system (600), either automatically or in response to a user entered command.

As shown in block (1018), the next step in process (1000) is to prepare biopsy system (102). Such initialization may include powering on biopsy system (102), allowing biopsy system (102) to perform self-diagnostics, calibrating biopsy system (102), and/or various other kinds of initialization tasks as will be apparent to those of ordinary skill in the art in view of the teachings herein. Other initialization tasks include, but are not limited to, adjusting room lighting, table orientation and height, pre-procedure cleaning, entering information on the chart and verification of personnel participating in the procedure. At this stage, the operator may also perform any other preparation that may be warranted with respect to any devices or materials within suite (10).

B. Exemplary Method of Acquiring and Storing Tissue Samples

Figure 9B:
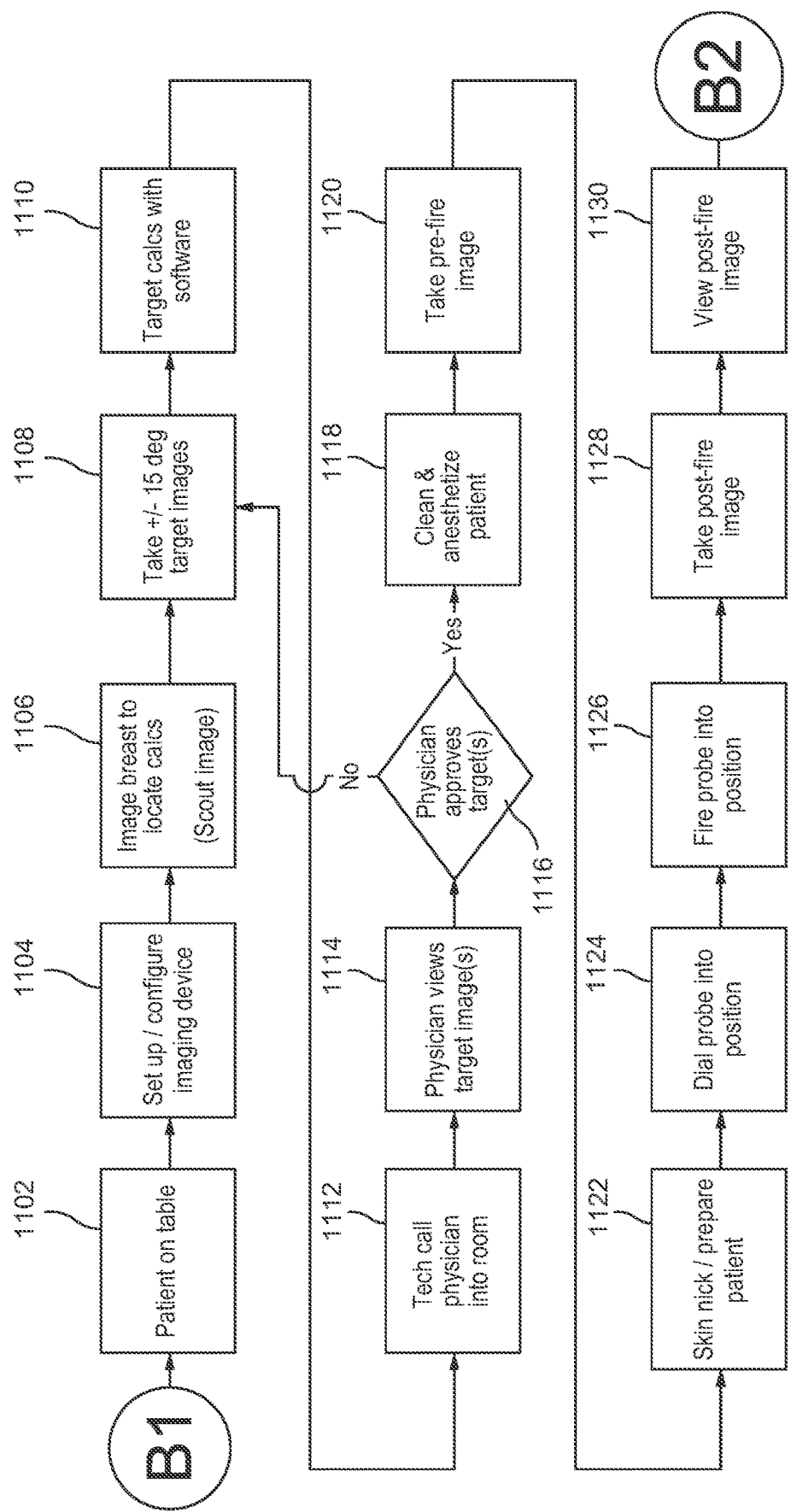
FIG. 9B depicts a flow chart showing a preliminary portion of an exemplary process for acquiring tissue samples with the stereographic biopsy suite of FIG. 1, the biopsy system of FIG. 2, the tissue sample tray of FIG. 3, the tissue imaging system of FIG. 4, the tissue container of FIG. 5, and the tissue tracking system of FIG. 8.

Upon completion of the preparation process (1000), the operator may transition to the tissue sample acquisition process (1100) as shown in FIG. 9B. As shown in block (1102), tissue sample acquisition process (1100) begins with placing the patient on patient table (24) and positioning the patient's breast in breast compression assembly (26). Next, as shown in outline form in block (1104), x-ray tube assembly (30) is set up and configured to provide imaging of the patient's breast in breast compression assembly (26).

With x-ray tube assembly (30) properly positioned, and as shown in block (1106), x-ray generator (2) is activated to provide a scout image of the patient's breast, to thereby search for calcifications within the breast tissue. Next, and as shown in block (1108), the operator acquires a pair of x-ray images—one being +15 degrees from the initial position and the other being −15 degrees from the initial position—to provide a stereotactic x-ray image of the patient's breast. Control module (40) then automatically evaluates the stereotactic x-ray image to identify calcifications in the tissue, as shown in block (1110). It should be understood that, as part of this process, control module (40) is operable to determine the location(s) of any calcification(s) within 3-dimensional space and thereby generate coordinates (e.g., Cartesian coordinates) that can be used to guide biopsy device (104) to the calcifications.

To the extent that the operator is not a physician (e.g., the operator is just a technician), the operator may call a physician into suite (10) to observe the calcifications on display screen (42), as shown in block (1112). The physician may then observe the calcifications on display screen (42), as shown in block (1114). If the physician does not feel that the image on display screen (42) provides a sufficient view of calcifications, or if the physician otherwise does not approve of the targeting suggested by control module (40), the physician may disapprove. This may result in the acquisition of another stereotactic image as described above with reference to block (1108) and the subsequent steps.

If the physician approves of the image/targeting in block (1116), process (1100) may then proceed to cleaning and anesthetizing the patient, as shown in block (1118). The operator may then activate control module (40) and x-ray generator (2) to take a pre-fire image of the patient's breast, as shown in block (1120). This pre-fire image may provide a reference with a particular viewing angle and position. As described below, a subsequent image may be compared against this reference image after needle (112) is fired into the patient's breast.

Next, the physician may form a skin nick (e.g., use a scalpel to form a small incision) at the needle (112) insertion site in the patient's breast, and provide any other preparation that may be needed with respect to the patient, as shown in block (1122). The physician may then operate guide assembly (28) in order to properly position biopsy device (104) in relation to the patient's breast, as shown in block (1124). This positioning of biopsy device (104) may be performed based on coordinates generated by control module (40), as described above. Once guide assembly (28) has positioned biopsy device (104) at the proper position and orientation relative to the patient's breast, the physician may actuate biopsy device (104) to fire needle (112) into the patient's breast, as shown in block (1126). It should be understood that, as part of this needle firing step, tip (114) may pass through the nick formed in the patient's skin as described above with reference to block (1122). It should be understood that, from this point until the stage described below with reference to block (1190) in FIG. 9E, needle (112) may remain disposed in the patient's breast.

After needle (112) has been fired into the patient's breast, control module (40) and x-ray generator (2) are activated to take a post-fire image of the patient's breast, as shown in block (1128). It should be understood that needle (112) remains disposed in the patient's breast during the acquisition of this post-fire image. The physician (or some other operator) may then observe the post-fire image, as shown in block (1130), to confirm that needle (112) is appropriately positioned in relation to a calcification (or other anomaly) within the patient's breast. In particular, the physician (or some other operator) may look to determine whether lateral aperture (116) is positioned adjacent to the calcification (or other anomaly) within the patient's breast. It should also be understood that, as part of the observation of the post-fire image, the physician (or some other operator) may compare the post-fire image to the pre-fire image, described above.

Figure 9C:
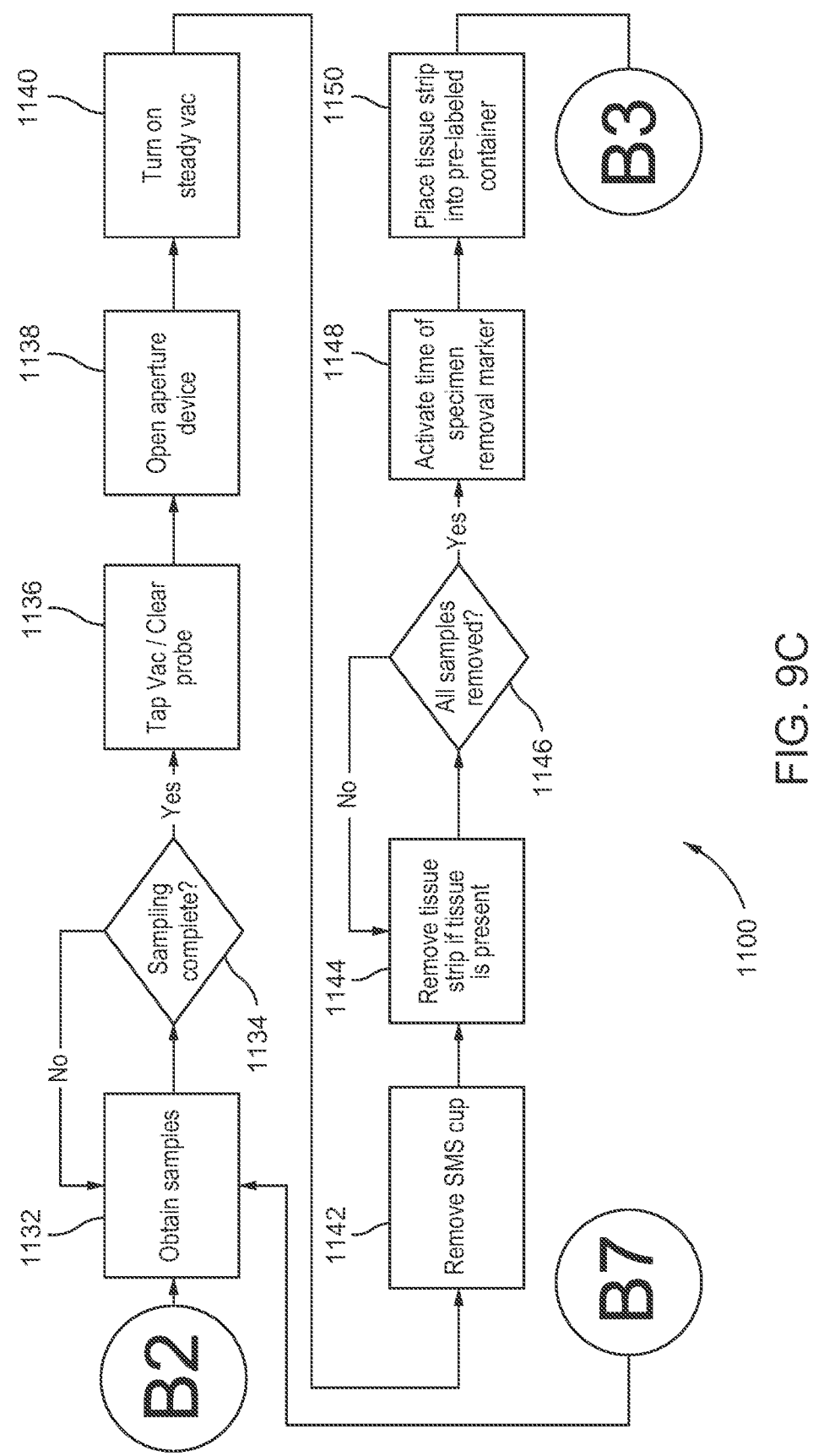
FIG. 9C depicts a flow chart showing another portion of an exemplary process for acquiring tissue samples with the stereographic biopsy suite of FIG. 1, the biopsy system of FIG. 2, the tissue sample tray of FIG. 3, the tissue imaging system of FIG. 4, the tissue container of FIG. 5, and the tissue tracking system of FIG. 8.
Figure 9D:
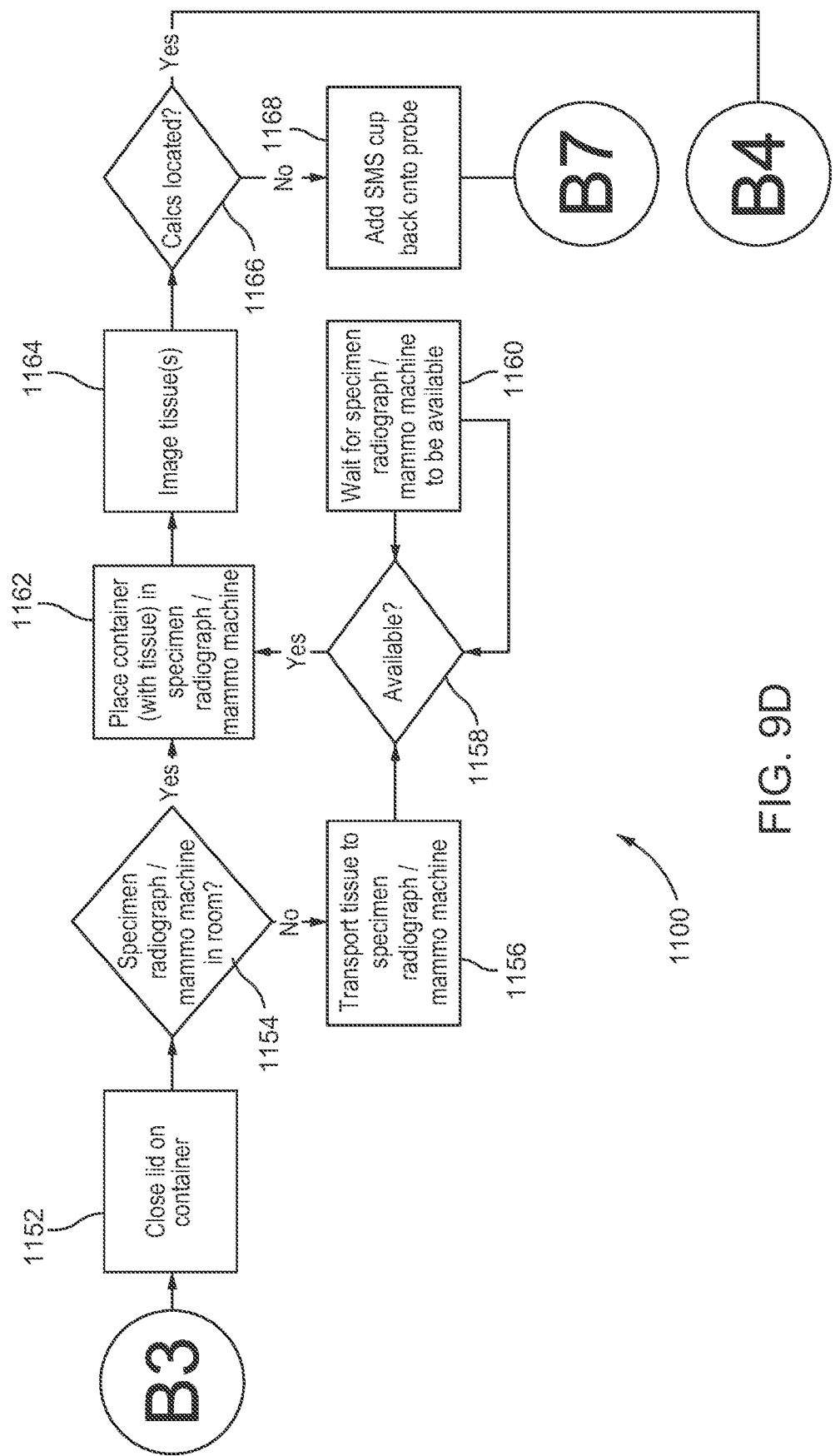
FIG. 9D depicts a flow chart showing a portion of an exemplary process for processing tissue samples with the stereographic biopsy suite of FIG. 1, the biopsy system of FIG. 2, the tissue sample tray of FIG. 3, the tissue imaging system of FIG. 4, the tissue container of FIG. 5, and the tissue tracking system of FIG. 8.

To the extent that the post-fire image indicates satisfactory placement of needle (112) in the patient's breast, process (1100) may continue to the steps shown in FIG. 9C. In particular, as shown in block (1132), the physician may operate biopsy system (102) to obtain one or more tissue samples. As noted above, these tissue samples may be deposited in respective strips (350) of receiving tray(s) (330) of tissue sample holder (130). The physician will determine whether a suitable number of tissue samples have been collected, as shown in block (1134), and will continue to obtain tissue samples until the desired number of tissue samples have been collected.

Once the desired number of tissue samples have been collected, biopsy system (102) is operated in a "clear probe" cycle, as shown in block (1136), to remove excess tissue particles, blood, and/or other debris from within probe (110). By way of example only, such a "clear probe" cycle may be performed in accordance with at least some of the teachings of U.S. Pub. No. 2014/0039343, entitled "Biopsy System," published on Feb. 6, 2014, the disclosure of which is incorporated by reference herein.

Upon completion of the "clear probe" cycle, the cutter is retracted proximally to open lateral aperture (116) of needle (112), as shown in block (1138). Biopsy system (102) is then operated to provide a "steady vac" state, as shown in block (1140), to remove excess blood from the biopsy site. By way of example only, such a "steady vac" state may be performed in accordance with at least some of the teachings of U.S. Pub. No. 2014/0039343, entitled "Biopsy System," published on Feb. 6, 2014, the disclosure of which is incorporated by reference herein.

While biopsy system (102) remains in a "steady vac" state, the physician (or some other operator) may then remove an outer cover of tissue sample holder (130), as shown in block (1142). With the cover removed, the physician (or some other operator) may then remove any receiving tray(s) (330) from tissue sample holder (130) that have tissue contained in corresponding strips (350), as shown in block (1144). The physician (or some other operator) may observe tissue sample holder (130) to determine whether all tissue samples have been removed, as shown in block (1146), and continue removing trays (330) until all tissue samples have been removed from tissue sample holder (130).

After all tissue samples have been removed from tissue sample holder (130), the operator may then immediately note the time at which the biopsy samples were captured by biopsy device (104), as shown in block (1148). By way of example only, this time notation may be made via tissue tracking system (600) and/or using any other suitable components. It should be understood that, by noting the time so contemporaneously to the actual time at which the biopsy samples were captured (i.e., rather than noting the time later, when the operator's memory of the tissue acquisition time might not be as accurate), it will allow a more accurate monitoring of the cold ischemic time of the tissue samples. In some versions, the time notation step represented by block (1148) is performed automatically. For instance, biopsy device (102) may be in communication with tissue tracking system (600), and may thereby transmit time stamps or other data each time the cutter is actuated to sever tissue (or each time the tissue sample holder is rotated to index another tissue receiving chamber relative to the cutter, etc.), to thereby provide an automatic indication of tissue sample acquisition time. Other suitable ways in which the tissue sample acquisition time may be noted at this stage, automatically or otherwise, will be apparent to those of ordinary skill in the art in view of the teachings herein.

Next, as shown in block (1150), the operator places the removed trays (330) in respective containers (500). As noted above, these containers (500) have already been labeled in accordance with the step shown in block (1004). The operator closes the lid (510) of each container (500), as shown in block (1152) of FIG. 9D, to thereby contain trays (330) in corresponding containers (500).

The next step of process (1100) will depend on whether imaging system (400) is located in biopsy suite (10), as shown in block (1154). If imaging system (400) is not located in biopsy suite (10), the operator will transport the containers (500) containing the tissue samples to an imaging system (400), as shown in block (1156). As shown in block (1158), the next step will depend on whether the imaging system (400) is available for use. If imaging system (400) is not available for use, the operator will simply have to wait for imaging system (400) to become available, as shown in block (1160). Once imaging system (400) becomes available, the operator may place one or more containers (500) in slot (414) of imaging system (400), as shown in block (1162). In some versions, slot (414) is configured to only receive one container (500) at a time, such that the operator will have to repeat the process separately for each container (500). In some other versions, slot (414) may accommodate more than one container (500), such that two or more containers (500) may be received in imaging system (400) simultaneously. It should also be understood that, in settings where imaging system (400) is located in suite (10), process (1100) may proceed directly to block (1162) from block (1154).

With one or more containers (500) located in imaging system (400), imaging device (412) may be activated to capture x-ray images of the tissue samples in the container(s) (500), as shown in block (1164). Based on the captured x-ray images, it may be determined whether any of the tissue samples have calcifications, as shown in block (1166). In some instances, this determination is made manually by a physician observing one or more x-ray images on display (418). In some other instances, the determination may be made automatically by data processor (416), based on data within the x-ray image(s). As yet another variation, data processor (416) may be configured to highlight potential calcifications based on data within the x-ray image(s), with the physician reaching the ultimate conclusion of whether the tissue in fact contains any calcifications.

Figure 9E:
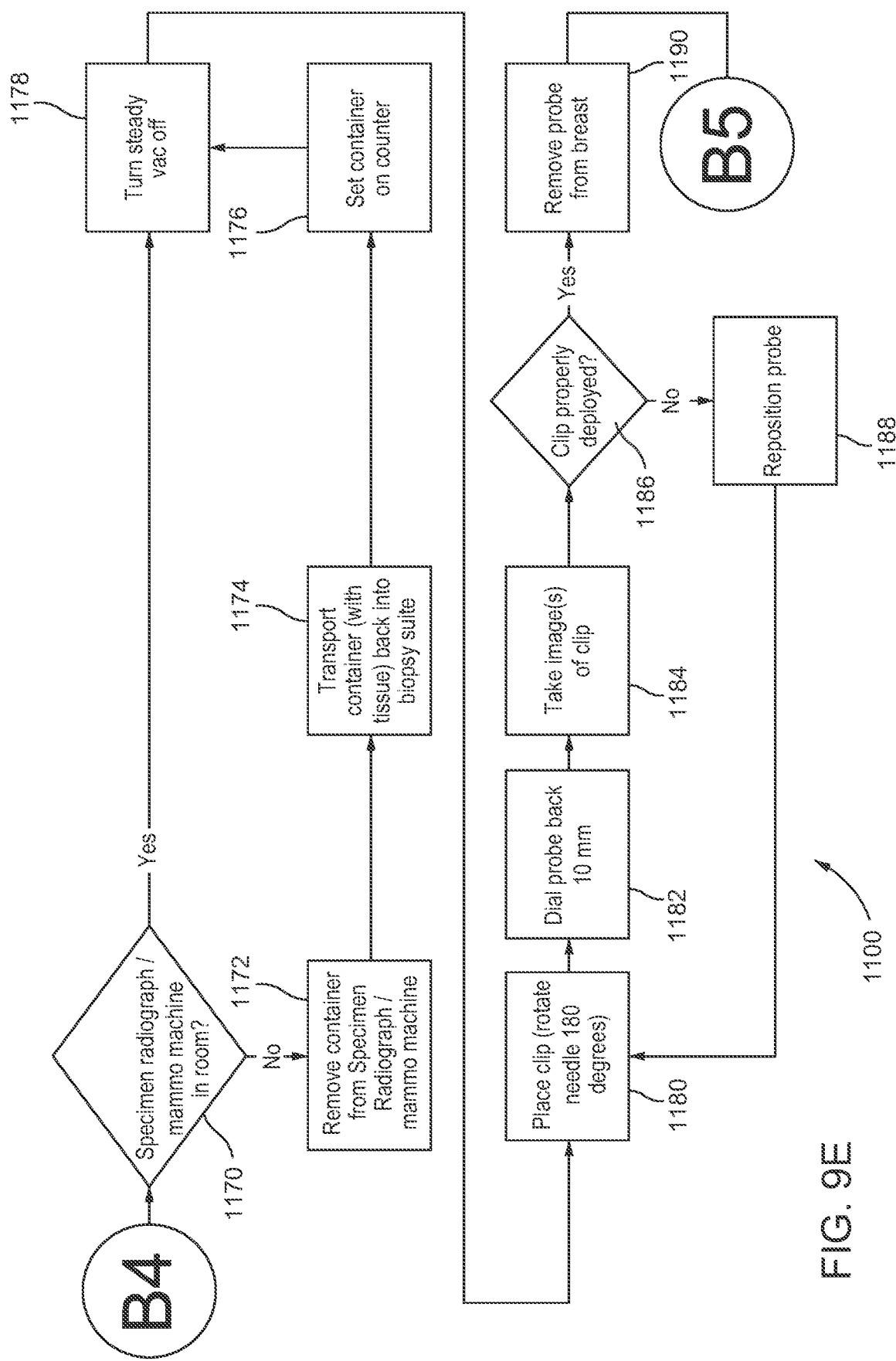
FIG. 9E depicts a flow chart showing another portion of an exemplary process for processing tissue samples with the stereographic biopsy suite of FIG. 1, the biopsy system of FIG. 2, the tissue sample tray of FIG. 3, the tissue imaging system of FIG. 4, the tissue container of FIG. 5, and the tissue tracking system of FIG. 8; and marking the biopsy site.

If calcifications are detected in block (1166), then process (1100) proceeds to block (1170) of FIG. 9E. If calcifications are not detected in block (1166), the physician (or some other operator) places the cover back on tissue sample holder (130), as shown in block (1168). Process (1100) then proceeds to block (1302) of FIG. 9H. As shown in block (1170), if calcifications are detected in block (1166), the next step again depends on whether imaging system (400) is located in suite (10). If imaging system (400) is not located in suite (10), then the next step is to remove container(s) (500) from imaging system (400), as indicated in block (1170). The container(s) (500) is/are then transported back to suite (10), as indicated in block (1174); and placed on a counter or other support surface in suite (10), as indicated in block (1176). The physician (or some other operator) then deactivates the "steady vac" state of biopsy system (102), as shown in block (1178). In settings where imaging system (400) is located in suite (10), then the physician (or some other operator) may proceed directly to deactivating the "steady vac" state of biopsy system (102) (i.e., avoiding the steps shown in blocks (1172, 1174, 1176)).

With the "steady vac" state deactivated, the physician may then insert a biopsy site marker applier into biopsy device (104) to deploy a biopsy site marker at the biopsy site via lateral aperture (116) of needle (112), as shown in block (1180). Such deployment of a biopsy site marker may be performed using known instruments and techniques. It should also be understood that the operator may rotate needle (112) approximately 180° about the longitudinal axis of needle (112) after deploying the biopsy site marker at the biopsy site. After deploying the biopsy site marker, the physician may actuate guide assembly (28) to retract biopsy device (104) proximally a predetermined distance (e.g., approximately 10 mm), as shown in block (1182). In some versions, the entire biopsy device (104) is retracted proximally the predetermined distance. In some other versions, just needle (112) is retracted proximally the predetermined distance, with at least some other portions of biopsy device (104) remaining stationary as needle (112) is retracted.

Next, the operator activates control module (40) and x-ray generator (2) to take an x-ray image of the patient's breast, to confirm whether the biopsy site marker was properly deployed, as shown in block (1184). Viewing the resulting x-ray image on display screen (42), the physician (or some other operator) determines whether the biopsy site marker was properly deployed, as shown in block (1186). In the event that the physician (or some other operator) determines that the biopsy site marker was not properly deployed, the physician (or some other operator) may reposition needle (112) and/or the rest of biopsy device (104), as shown in block (1188). By way of example only, this repositioning may include advancing needle (112) and/or the rest of biopsy device (104) distally the predetermined distance (e.g., approximately 10 mm). The physician (or some other operator) may then deploy another biopsy site marker at the biopsy site, as shown in block (1180). The physician (or some other operator) may then continue again through the steps shown in blocks (1182, 1184, 1186), and repeat until the physician (or some other operator) confirms that a biopsy site marker has been properly deployed at the biopsy site.

Once the physician (or some other operator) confirms that a biopsy site marker has been properly deployed at the biopsy site, the physician (or some other operator) may then remove needle (112) from the patient's breast, as shown in block (1190). It should be understood that needle (112) may have remained disposed in the patient's breast the entire time during performance of all of the steps shown in FIGS. 9B-9E, from the step represented by block (1126) to the step represented by block (1190). It should also be understood that performing all of these steps while needle (112) remains disposed in the patient's breast may provide efficiencies as will be understood by those skilled in the art in view of the teachings herein. It is understood that the design to retain the needle in the patient's breast or remove the needle is left up to the physician performing the procedure and is based on the patient specific information relative to the goal of the breast biopsy procedure. In other words, this part of the procedure is entirely dependent upon what the physician thinks, in his/her professional judgement is appropriate.

Figure 9F:
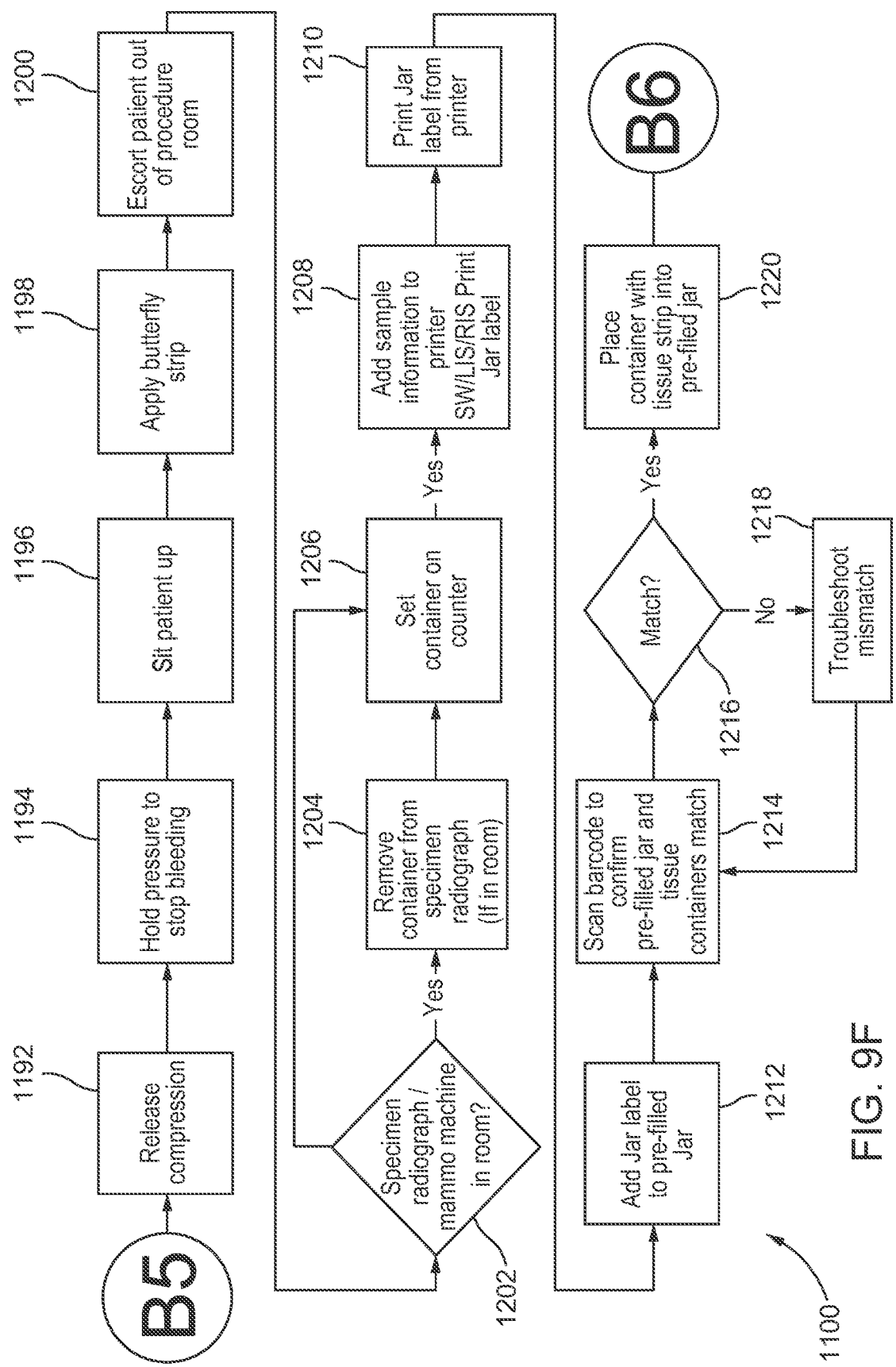
FIG. 9F depicts a depicts a flow chart showing an exemplary process of treating a patient and further processing of tissue samples acquired from the processes of FIGS. 9A-9E.

After needle (112) is removed from the patient's breast, and as shown in block (1192) of FIG. 9F, the physician (or some other operator) then actuates breast compression assembly (26) to release the patient's breast. The physician (or some other operator) then applies pressure to the patient's breast at the area where needle (112) was disposed, to stop bleeding, as shown in block (1194). The patient is then moved to a sitting position, as shown in block (1196); and a butterfly strip and/or other kind of treatment is applied to the needle (112) insertion site on the patient's breast, as shown in block (1198). The patient is then escorted out of suite (10), as shown in block (1200).

Once the patient has left suite (10), the next step depends on whether imaging system (400) is located within suite (10), as shown in block (1202). If imaging system (400) is located within suite (10), then container(s) (500) is/are removed from imaging system (400), as shown in block (1204). The removed container(s) (500) is/are then set on a counter or other support surface in suite (10), as shown in block (1206). In settings where imaging system (400) is not located within suite (10), then the container(s) (500) will have already been removed from imaging system (400) and placed on a counter or other support surface in suite (10), as noted above with reference to block (1176) of FIG. 9E.

Next, the operator adds information relating to the tissue samples in container (500) into tissue tracking system (600), as shown in block (1208). In addition, or in the alternative, at least some of the information relating to the tissue samples in container (500) may be electronically transmitted to tissue tracking system (600). By way of example only, imaging system (400) may be in communication with tissue tracking system (600) and may thereby automatically communicate information obtained during the imaging steps described above. In either scenario, the operator may include annotations relating to specific strips (350) (e.g., identifying specific strips (350) having tissue with identified calcifications, etc.).

Once the appropriate information has been entered into tissue tracking system (600), printer (620) may be activated to print a label for transport container (550), as shown in block (1210). It should be understood that this label may contain more information than the information contained in the labels produced during the step shown in block (1002) since the printing step shown in block (1210) is performed after tissue has been captured by biopsy system (102) and analyzed by imaging system (400).

After a label has been printed for transport container (550), the label may be applied to transport container (550), as shown in block (1212). In the present example, transport container (550) is provided pre-filled with a fixative. One common example of a fixative is formalin, although other solutions may be used such as saline. Next, the operator operates scanner (630) of tissue tracking system (600) to scan a barcode, RFID tag, or other kind of tag on the label that was applied to transport container (550), as shown in block (1214). The operator also operates scanner (630) of tissue tracking system (600) to scan a barcode, RFID tag, or other kind of tag on the label that was applied to the container (500) that the operator intends to place in transport container (550), as also shown in block (1214).

After the barcodes/tags of transport container (550) and container (500) have been scanned, control unit (610) evaluates the scanned barcodes/tags to determine whether there is a match between the barcodes/tags, as shown in block (1216). For instance, control unit (610) may confirm whether the barcodes/tags relate to the same patient and/or the same biopsy procedure, etc. In some examples, this evaluation may include communication with a laboratory information system to obtain data loaded in connection with block (1016) or block (1208). In the event that there is a mismatch or other discrepancy, the operator may troubleshoot the problem, as shown in block (1218), and re-scan if warranted. However, if control unit (610) confirms a match between the label on transport container (550) and the label on container (500), tissue tracking system (600) may notify the operator of the match. The operator may then place container (500) in transport container (550) and seal transport container (550), as shown in block (1220).

It should be understood that, by labeling container (500) at the beginning of the process, and then comparing the label of container (500) with the label of transport container (550), the risk of mishandling of tissue samples may be reduced. For instance, the dual label system may reduce the risk of one patient's tissue samples being placed in a transport container (550) that is intended for another patient. Moreover, having the second label printed for transport container (550) may allow additional information to be consistently included on transport container (550), without having to rely on neatness of a person's handwriting as may be the case where such labels are written on by hand. The dual label system also doubles the chances of errors being caught by personnel reading the labels and the bar code can be programmed such that if the dual labels do not match, the tissue processing software will not allow the specimen to be further processed.

Figure 9G:
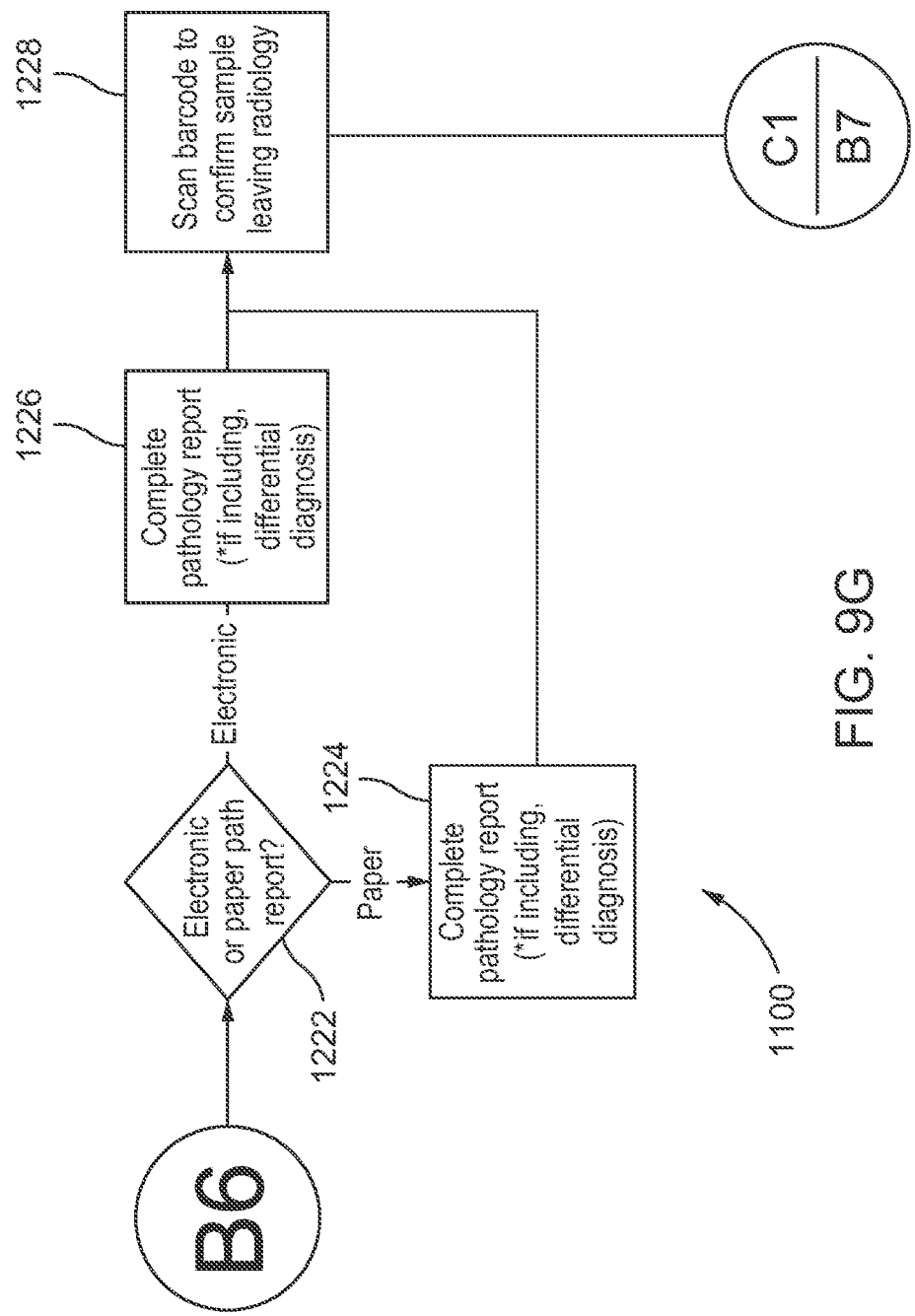
FIG. 9G depicts a depicts a flow chart showing an exemplary process for handling data associated with the acquisition and processing of tissue samples acquired from the processes of FIGS. 9A-9F.
Figure 9I:
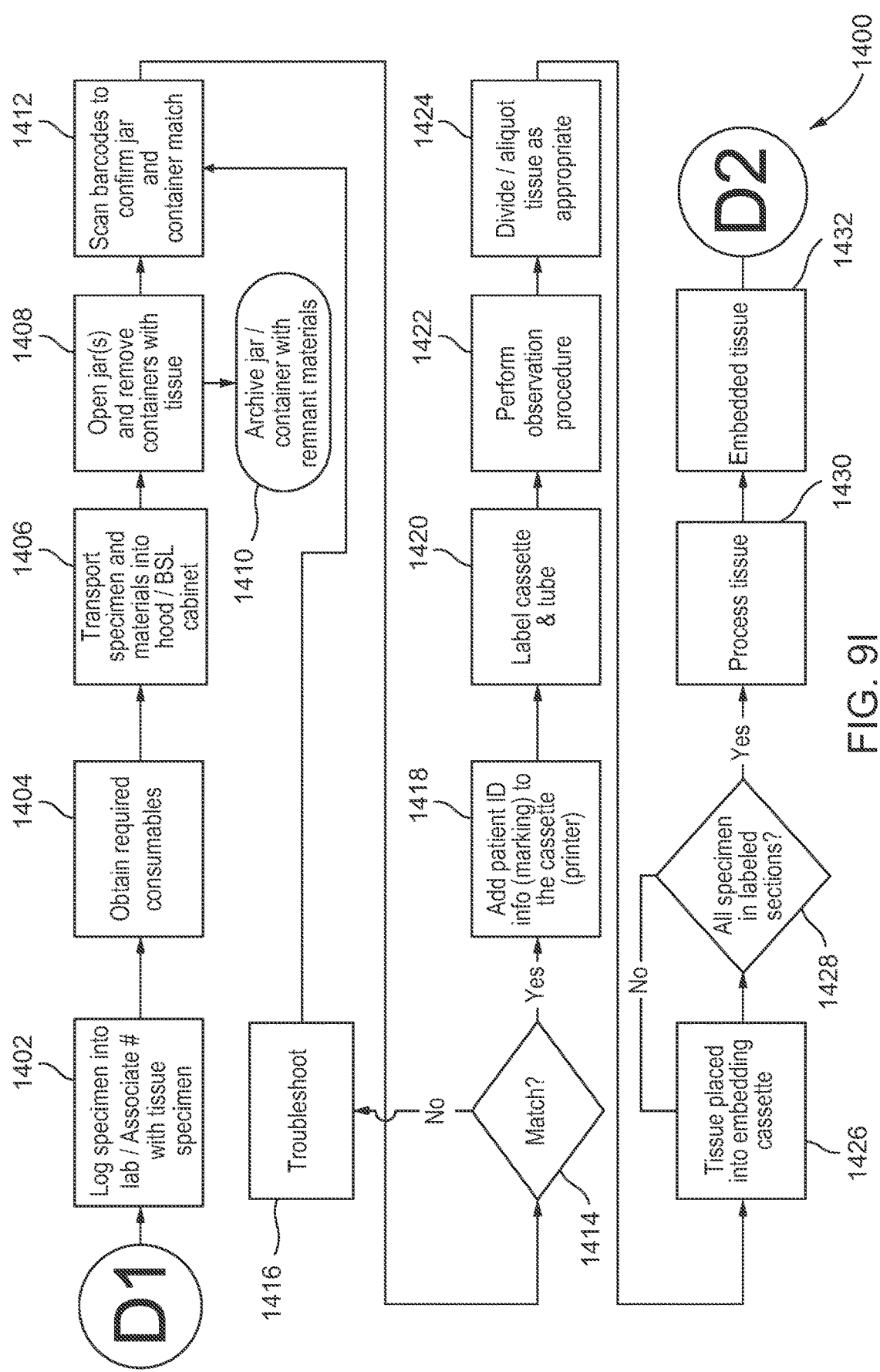
FIG. 9I depicts a flow chart showing an exemplary process of further processing tissue samples acquired from the processes of FIGS. 9A-9H.
Figure 9J:
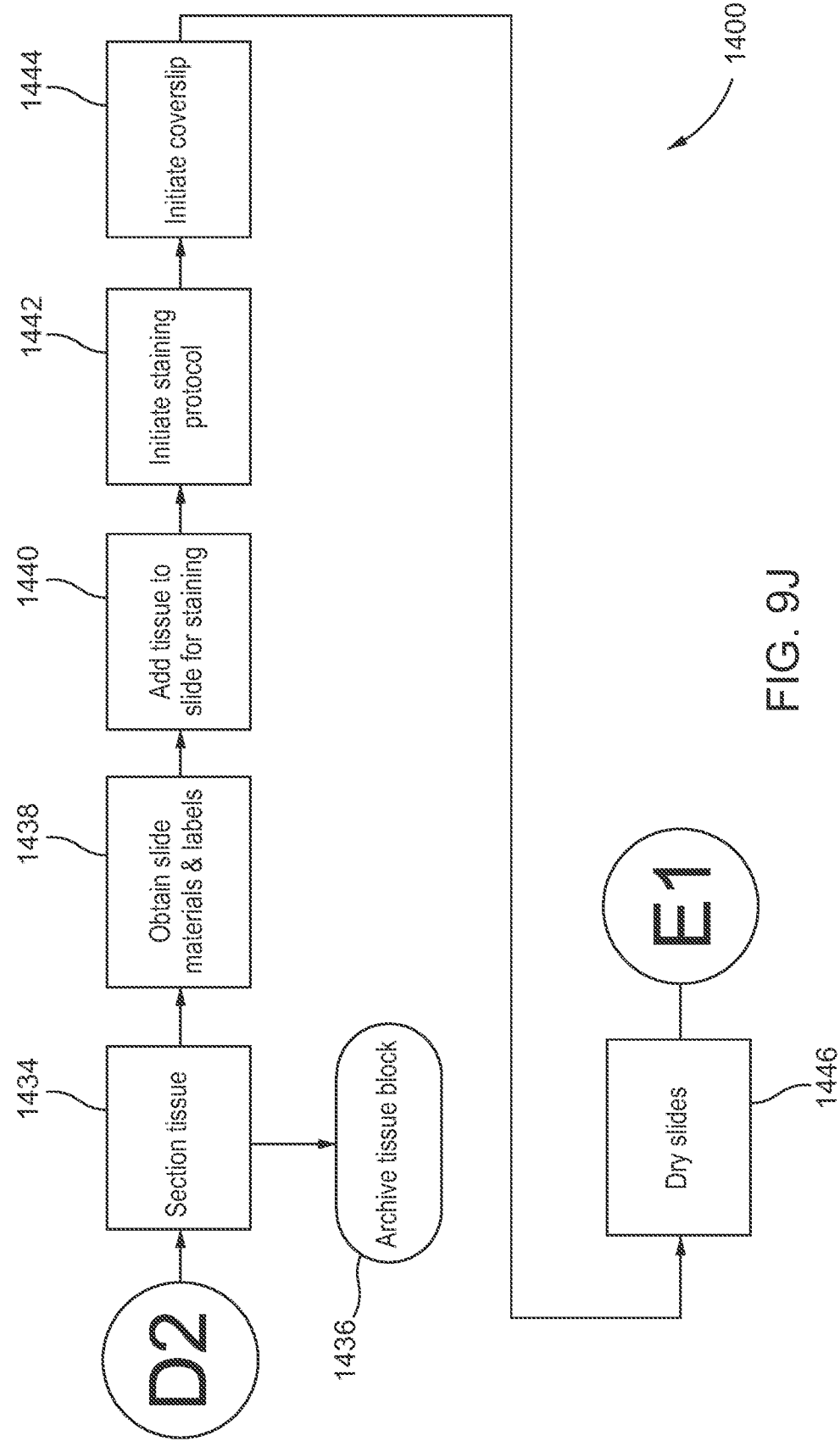
FIG. 9J depicts a flow chart showing an exemplary process of further processing tissue samples acquired from the processes of FIGS. 9A-9I.
Figure 9K:
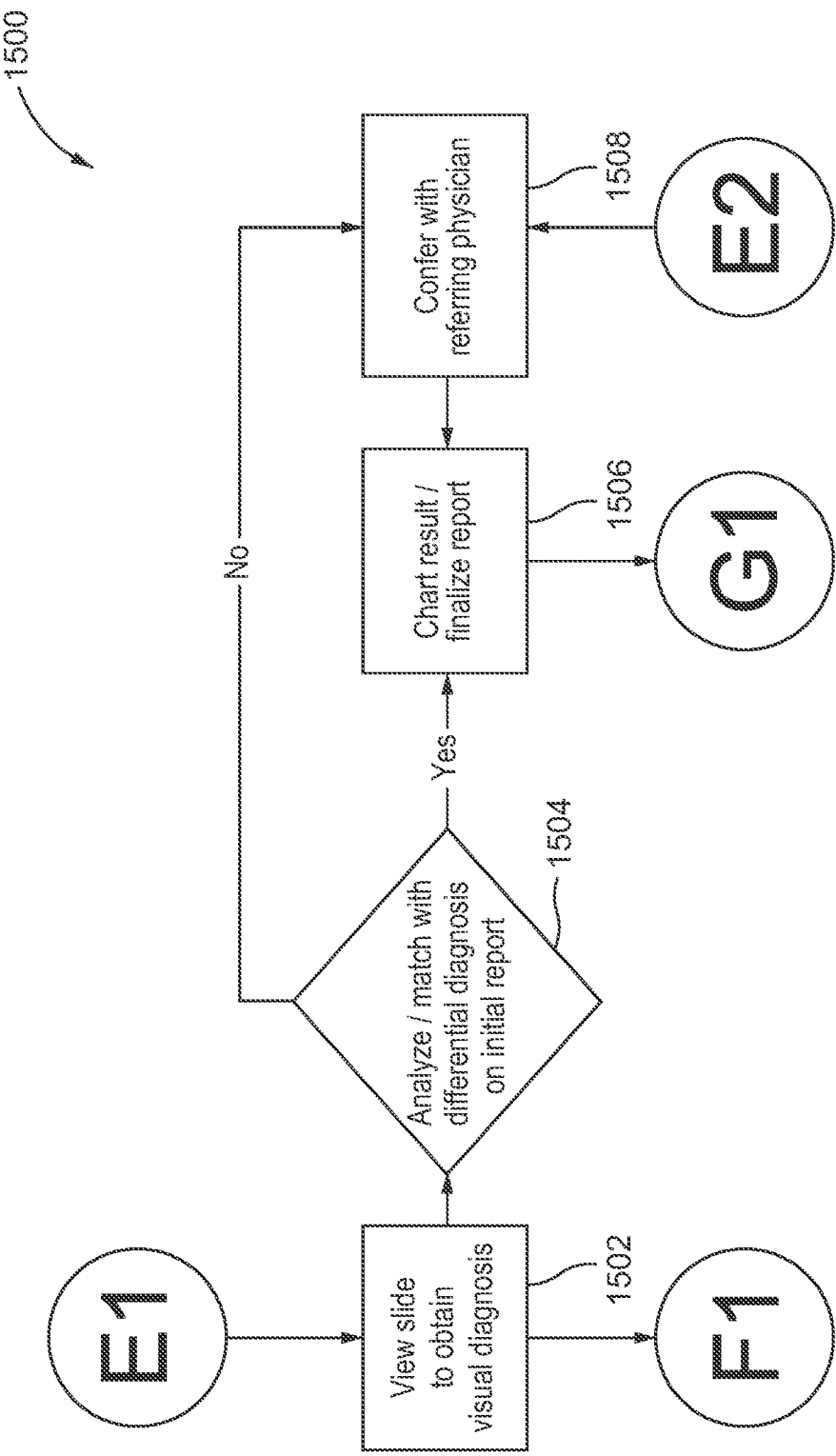
FIG. 9K depicts a flow chart showing an exemplary process of further processing tissue samples acquired from the processes of FIGS. 9A-9J.
Figure 9L:
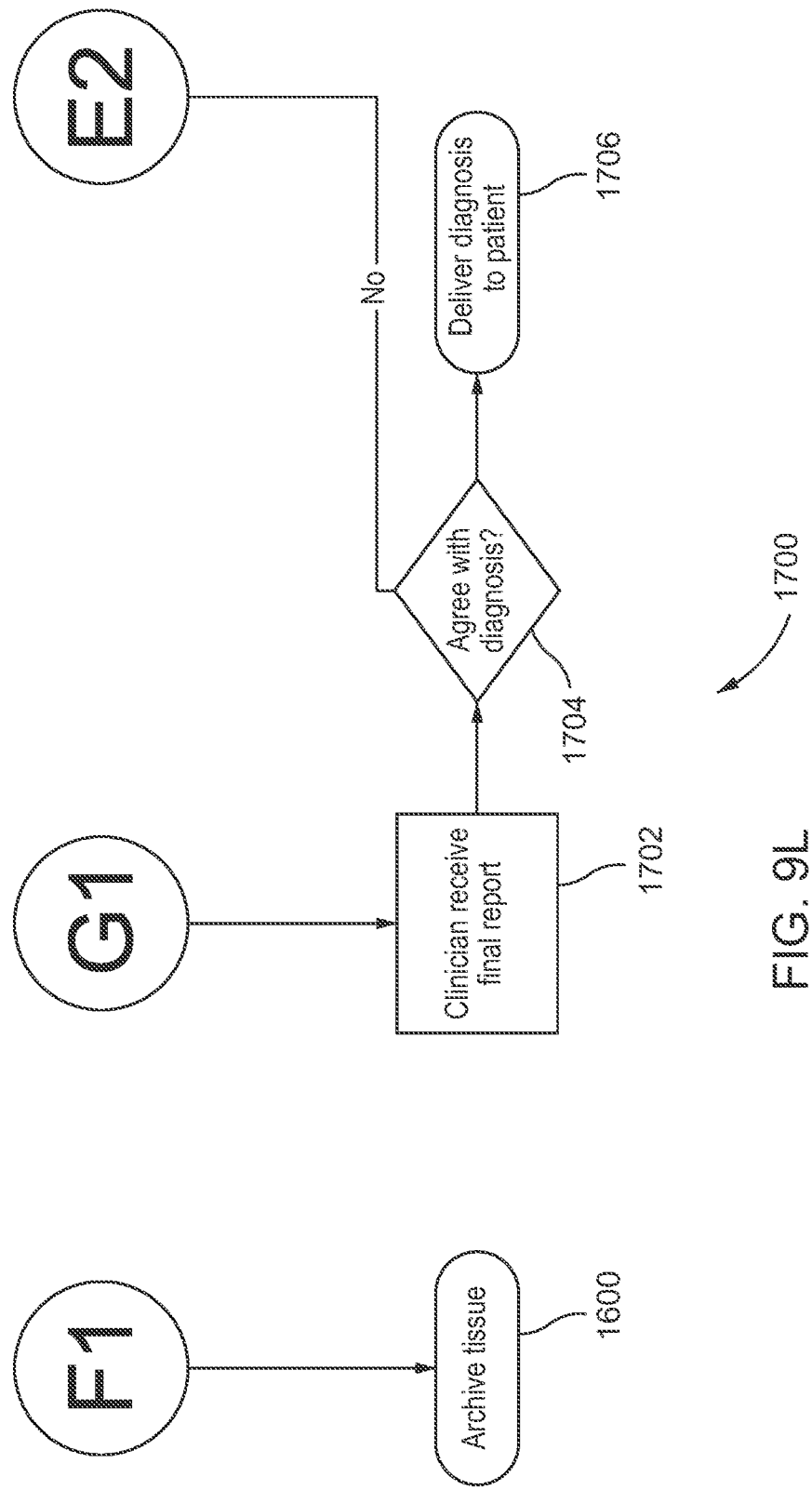
FIG. 9L depicts a flow chart showing an exemplary process of archiving tissue, and confirming and delivering results to a patient, following the processes of FIGS. 9A-9K.

With container (500) sealed in transport container (550), the operator may then interact with user interface feature (612) of tissue tracking system (600) to indicate whether to generate an electronic or paper radiology report, as shown in block (1222) of FIG. 9G. In the very rare modern biopsy procedures now being conducted, if the operator selects a paper radiology report, tissue tracking system (600) may be used to generate a paper radiology report via printer (620), as shown in block (1224). The use of paper radiology reports is very rare in modern procedures. In some versions, the printed radiology report includes a barcode or other tag that may be scanned to confirm that it matches with a particular transport container (550). Although this is not a current procedure, at this point in the process, optionally, if the operator selects an electronic radiology report, tissue tracking system (600) may be used to generate an electronic radiology report, as shown in block (1226). The electronic pathology report may be transmitted to an appropriate computer or other device in communication with tissue tracking system (600), using any suitable form of electronic communication.

Regardless of whether the operator selected an electronic or paper pathology report, the operator may then use scanner (630) to scan the label or tag on transport container (550), to confirm that the tissue samples are leaving radiology processing, as shown in block (1228).

C. Exemplary Tissue Transportation Process

Upon leaving radiology processing, the transport container (550) containing tissue samples in container (500) may be put in a transportation process (1300), as shown in FIG. 9H. In particular, the transport container (550) containing tissue samples in container (500) may be transported to a pathology lab, as shown in block (1302). In the event that the operator selected a paper radiology report in block (1222), the paper report may accompany the transport container (550). In the event that the operator selected an electronic radiology report in block (1222), the electronic radiology report may be electronically communicated to the pathology lab via a laboratory information system, such that the electronic radiology report may be received before the transport container (550) is received.

When transport container (550) is received at the pathology lab, an operator at the pathology lab may scan the label or tag on transport container (550) to confirm receipt of the transport container (550). By way of example only, the pathology lab may have its own tissue tracking system (600). In some versions, the equipment that the person uses at the pathology lab to scan the label or tag on transport container (550) is in communication with the tissue tracking system (600) that is located in suite (10) or the radiology lab associated with suite (10), such that the tissue tracking system (600) that is located in suite (10) or the radiology lab associated with suite (10) receives an electronic notification indicating that transport container (550) has arrived at the pathology lab. In addition, this notification may serve as a "handshake" that initiates the automatic transfer of information from tissue tracking system (600) to the equipment that the person uses at the pathology lab to scan the label or tag on transport container (550). For instance, this "handshake" may trigger tissue tracking system (600) to automatically transmit the electronic radiology report generated during the step represented by block (1226).

After completing the intake scanning of transport container (550), the pathology laboratory may then proceed with additional processing and fixation, as indicated generally by block (1306).

D. Exemplary Pathology Process

The processing referred to above with respect to block (1306) is shown in further detail as pathology process (1400) in FIGS. 9I-9J. In particular, FIG. 9I shows pathology process (1400) starting with the logging of the tissue samples into the pathology lab as block (1402). As part of this logging step, an identification number or other form of identification may be associated with the tissue samples. This logging and association may be performed using a form of tissue tracking system (600) at the pathology lab and/or using any other suitable equipment. The operator may then obtain any required consumables, as shown in block (1404). By way of example only, such consumables may include biopsy/embedding cassettes, stains, paraffin, microtome blades, slides, other dissection instruments, mounting media and adhesives, reagents and solutions, gloves, and/or other consumables as will be apparent to those of ordinary skill in the art in view of the teachings herein.

Next, the operator will transport the tissue samples, which are still in transport container (550) at this stage, to a processing area under a hood or in a biosafety cabinet, as shown in block (1406). The operator will then open transport container (550) and remove the container(s) (500) from transport container (550), as indicated in block (1408).

The operator will then scan the labels or tags on transport container (550) and on the container(s) (500) that was/were removed from transport container (550), as shown in block (1412). This may be performed using a scanner (630) of a version of tissue tracking system (600) that is located at the pathology lab. Alternatively, any other suitable hardware may be used. Optionally, the operator may archive transport container (550) and any materials that remain in transport container (550), as shown in block (1410).

Based on the scanned labels or tags on transport container (550) and on the container(s) (500) that was/were removed from transport container (550), control unit (610) will determine whether there is a match, as shown in block (1414). It should be understood that the matching performed in block (1414) is the same as the matching performed in block (1216), described above. In the event that there is a mismatch, the operator may troubleshoot the mismatch, as shown in block (1416), then re-scan as shown in block (1412). In the event that there is a match, the operator may then add patient identification information to one or more biopsy/embedding cassettes, as shown in block (1418). By way of example only, this may include activating printer (620) of tissue tracking system (600) to print a label that may be applied to a label surface of a biopsy/embedding cassette. The patient identification may be provided in the form of an alphanumeric code, an optical code, and/or in any other suitable form. The operator may then apply the label to the biopsy/embedding cassette and optionally to a tissue storage tube as shown in outline form in block (1420).

With the biopsy/embedding cassette and tube labeled, the operator then performs an observation procedure, such as "macroscopic grossing" as shown in block (1422). The operator then removes the tissue samples from container (500) and divides or aliquots the tissue samples as appropriate, as shown in block (1424). The operator then places the divided/aliquoted tissue into the labeled biopsy/embedding cassette, as shown in block (1426). As indicated in block (1428), this continues until all of the tissue of interest is placed in one or more labeled biopsy/embedding cassettes.

Once all of the tissue of interest has been placed in one or more labeled biopsy/embedding cassettes, the operator then performs additional processing of the tissue, as indicated in block (1430). By way of example only, this additional processing may include dehydration, clearing, and infiltration. Various suitable ways in which such processing may be carried out will be apparent to those of ordinary skill in the art in view of the teachings herein. Once this processing is complete, the operator may provide embedding of the tissue, as indicated in block (1432). This embedding may include embedding the tissue in paraffin, as is known in the art.

After the tissue has been embedded, the tissue may then be sectioned as indicated in block (1434) of FIG. 9J. This sectioning may be performed using a microtome device and/or any other suitable equipment. If desired, the tissue block may be archived as shown in block (1436). After the tissue has been sectioned, the operator may obtain slide materials and labels as shown in block (1438). The operator may then add the section tissue to the slides, as shown in block (1440). Next, the operator may initiate a staining protocol on the tissue that is located on the slides, as shown in block (1442). Various suitable materials and techniques that may be used to perform such staining will be apparent to those of ordinary skill in the art in view of the teachings herein. With the sectioned tissue stained on the slides, the operator may then initiate coverslips on the tissue, as indicated in block (1444); then allow the slides to dry, as indicated in block (1446).

E. Exemplary Diagnosis Process

After the slides have dried, the diagnosis process (1500) may begin as shown in FIG. 9K. In particular, diagnosis process (1500) begins with the pathologist viewing the slide to obtain a visual diagnosis, as shown in block (1502). The pathologist will then compare this visual diagnosis to the differential diagnosis provided on the initial pathology report, as indicated in block (1504). It should be understood that this initial pathology report is the report referred to above with reference to blocks (1222, 1224, 1226) of FIG. 9G, which was either prepared at the radiology lab or prepared elsewhere based at least in part on data from the radiology lab. In other words, in block (1504), the pathologist may optionally check their diagnosis with other physicians, such as other pathologists, oncologists, etc. etc.

If the comparison of block (1504) reveals consistency between diagnoses, the pathologist may chart the result and finalize the initial pathology report, as shown in block (1506). If the comparison of block (1504) reveals consistency between diagnoses, the pathologist may confer with the referring physician to attempt to resolve the inconsistency, as shown in block (1508). Based on this consultation with the referring physician, the pathologist may chart the result and finalize the initial pathology report, as shown in block (1506).

As shown in block (1600) of FIG. 9L, the pathologist may archive the tissue after viewing the slide to obtain a visual diagnosis (block (1502)). Various suitable ways in which the tissue may be archived will be apparent to those of ordinary skill in the art in view of the teachings herein.

F. Exemplary Tissue Storage and Diagnosis Delivery Process

As is also shown in FIG. 9L, a diagnosis delivery process (1700) may begin with the pathology report being sent to the clinician at biopsy suite (10), as shown in block (1702). It should be understood that this pathology report is the same report described above as being finalized in block (1506). The clinician may then decide whether they agree with the diagnosis in the pathology report, as shown in block (1704). If the clinician does not agree with the diagnosis in the pathology report, the clinician may confer with the referring physician, as shown in block (1508) and as described above with reference to FIG. 9K. If the clinician does agree with the diagnosis in the pathology report, the clinician may deliver the diagnosis to the patient, as shown in block (1706).

VII. Exemplary Alternative Components and Methods

Figure 10:
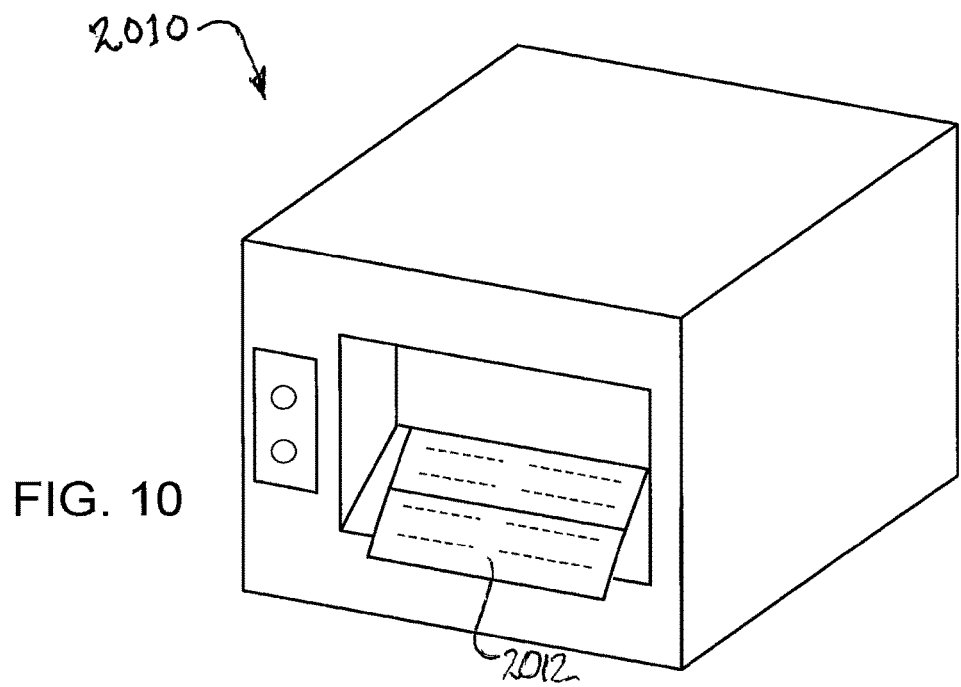
FIG. 10 depicts a perspective view of an exemplary label printer for a tissue container.

FIGS. 10-23 show various alternative components and methods that may be used with processes (1000, 1100, 1300, 1400, 1500, 1700) described above. For instance, FIG. 10 shows a label printer (2010) that may be readily usable with a tissue container (500) or another tissue container (2500) as will be described in greater detail below. Label printer (2010) of the present example is generally configured to print one or more labels (2012) on specialized pre-configured label blanks. In some examples, label printer (2010) is a conventual commercially available printer as will be apparent to those of ordinary skill in the art in view of the teachings herein. In the context of the processes (1000, 1100, 1300, 1400, 1500, 1700) described above, label printer (2010) can be used in the procedure room itself, or in a near-by room, or even in the pathology lab area where a whole stack of tissue containers (500, 2500) could be labeled before the start of a busy day of conducting breast biopsy procedures. By way of example only, label printer (2010) may be used in connection with any one or more of steps (1002, 1210, 1418) described above.

Figure 11:
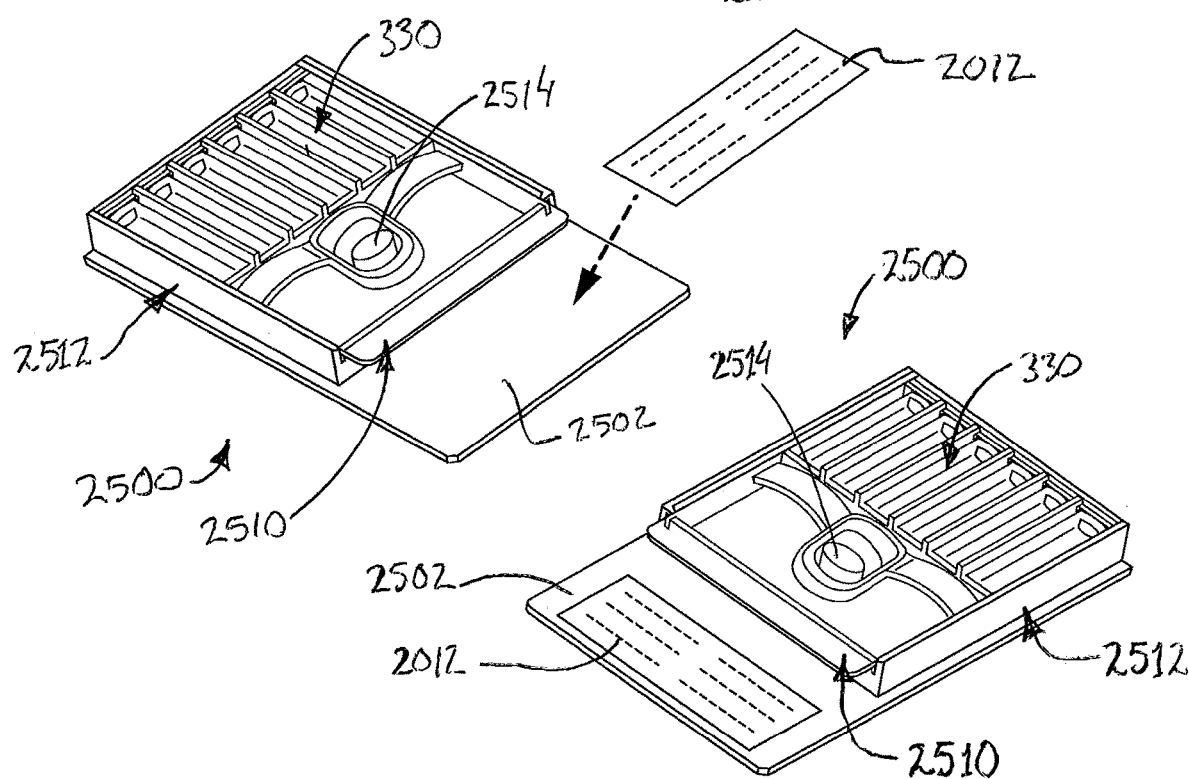
FIG. 11 depicts a perspective view of a label being adhered to a label surface of a tissue container.

FIG. 11 shows a label (2012) being adhered to a label surface (2502) of a tissue container (2500) after label (2012) was printed using label printer (2010). In the context of the processes (1000, 1100, 1300, 1400, 1500, 1700) described above, label (2012) can be adhered to tissue container (500, 2500) in the procedure room itself, or in a near-by room, or even in the pathology lab area where a whole stack of tissue containers (500, 2500) could be labeled before the start of a busy day of conducting breast biopsy procedures. By way of example only, label (2012) may be used in connection with any one or more of tissue containers (500, 2500) or jar during any one or more of steps (1004,1212, 1420) described above.

Figure 13:
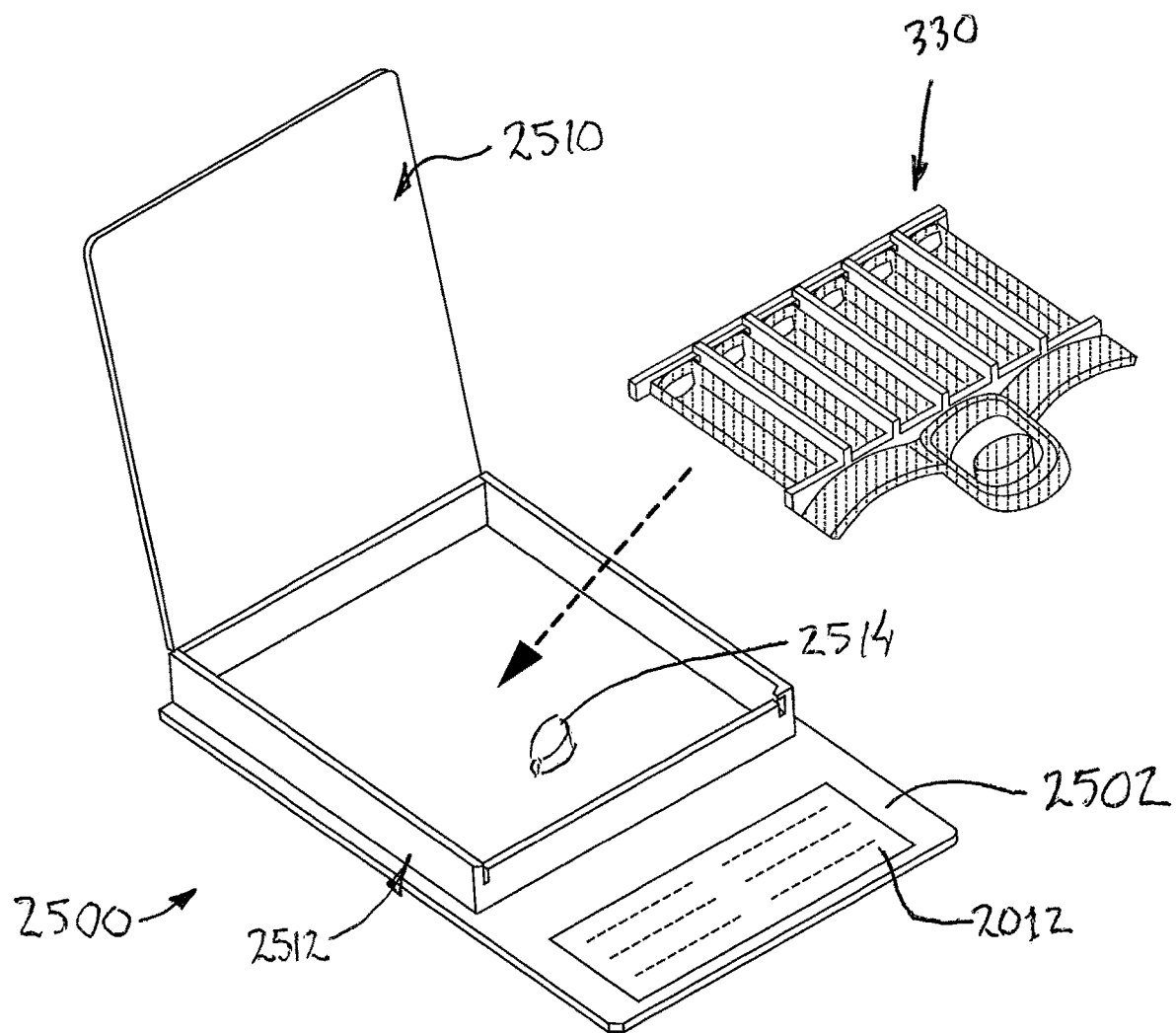
FIG. 13 depicts a perspective view of the tray of FIG. 12, now flattened into a flat configuration being placed into a tissue container.
Figure 13:

Tissue container (2500) is best seen in FIGS. 11 and 13. As described above, tissue container (2500) is generally substantially similar to tissue container (500) described above. For instance, like with tissue container (500), tissue container (2500) comprises a base (2512) and a cover (2510). In the present example, base (2512) is sized to receive tray (330) in a flattened configuration. Cover (2510) is coupled with base (2512) such that cover (2510) is pivotable relative to base (2512). Accordingly, cover (2510) may be opened relative to base (2512) to allow base (2512) to receive tray (330), as shown in FIG. 13; and cover (2510) may then be closed relative to base (2512) to enclose tray (330) within container (2500) for imaging. Alternatively, in some examples cover (2510) is slidable into a one or more integral slots disposed within base (2512) to permit selective coupling and decoupling of cover (2510) relative to base (2512) to insert tray (330) within base (2512). Cover (2510) of the present example comprises a transparent material to allow for optical imaging or other optical observation of tissue samples within tray (330). Although not shown, it should be understood that in other examples base (2512) can also be made of a transparent material to allow for optical imaging or other optical observation of the tissue samples within tray (330)

Base (2512) comprises a tab (2514) extending upwardly towards cover (2510). Tab (2514) is configured to receive at least a portion of tray (330) to thereby hold tray (330) within base (2512). Tab (2514) thereby maintains tray (330) in the flattened configuration for imaging. In the present example, the end portion of tab (2514) generally relies on a compression fit to hold tray (330), although in other versions alternative coupling configurations can be used. By way of example only, other alternative features of tissue container (2500) may be configured in accordance with at least some of the teachings of U.S. Ser. No. 15/638,740, entitled "Biopsy Sample Container," filed on an even date herewith, the disclosure of which is incorporated by reference herein.

Figure 12:
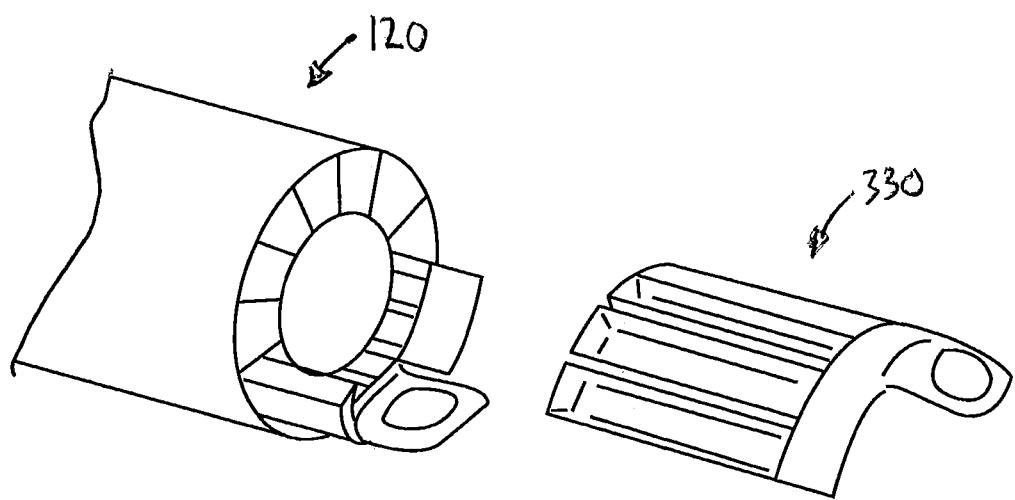
FIG. 12 depicts a perspective view of a tray being removed from a tissue sample holder of the biopsy system of FIG. 2.

FIGS. 12-14A show an exemplary procedure for preparing tray (330) and tissue container (2500) for imaging. By way of example only, the procedure shown in FIGS. 12-14A may be used in connection with procedure (1100) at bocks (1142, 1144, 1146, 1148, and 1150) described above. For instance, one at least one tissue sample has been collected in tissue sample holder (130) of biopsy system (102), a single tray (330) can be removed by an operator from at least a portion of tissue sample holder (130) as shown in FIG. 12.

Figure 14A:
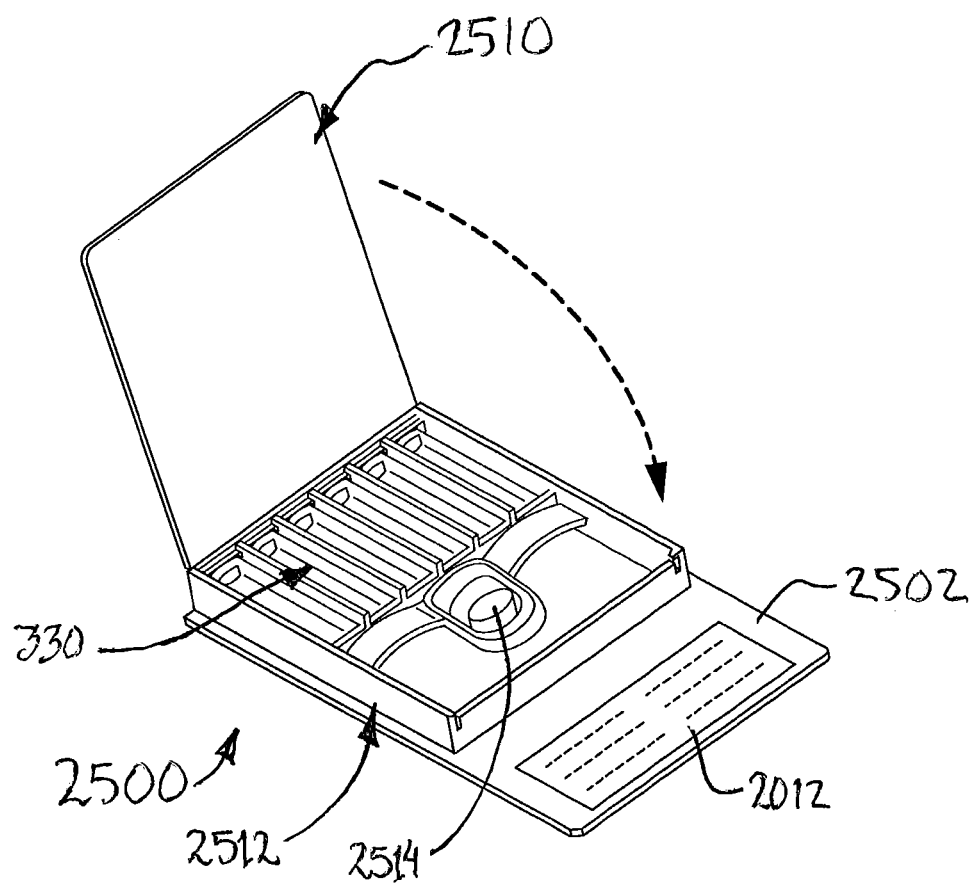
FIG. 14A depicts a perspective view of a lid of the tissue container of FIG. 13 being closed in the direction of the arrow.

Once tray (330) is removed from tissue sample holder (130), an operator can transport tray (330) into close proximity with tissue container (2500). It should be understood that at this stage tissue container (2500) is pre-labeled with label (2012) including various patient information. Alternatively, label (2012) may be affixed after placement of tray (330) within container such that label (2012) may include certain information specific to the samples received within tray (330). In either case, tray (330) can next be loaded into tissue container (2500) as shown in FIG. 13. Cover (2510) is then closed as shown in FIG. 14A.

Figure 14B:
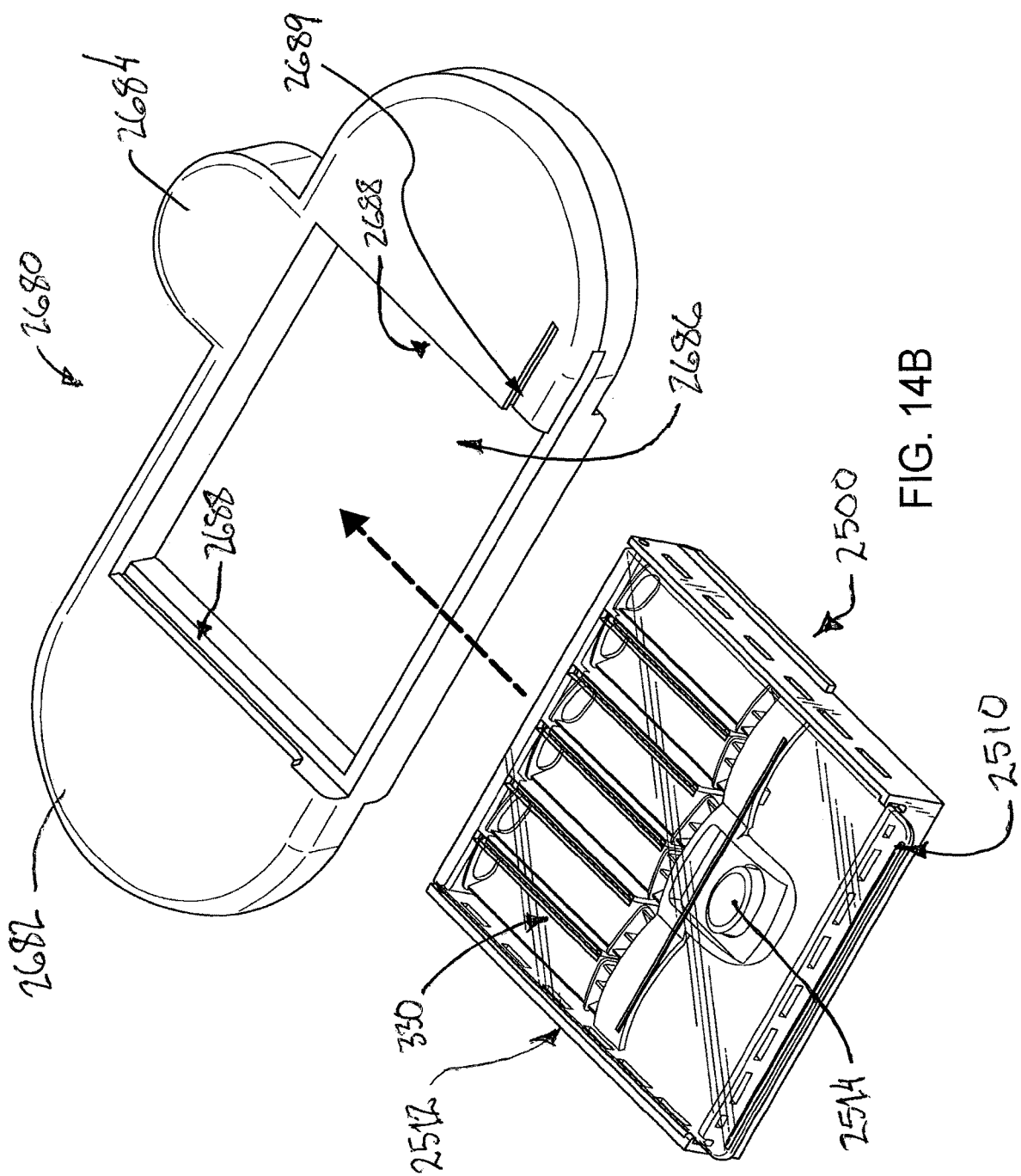
FIG. 14B depicts a perspective view of the tissue container of FIG. 13 being positioned for engagement with an adaptor.

Once tray (330) is loaded into tissue container (2500) the combination of tray (330) and container (2500) may be loaded into an adaptor (2680) for imaging. As shown in FIG. 14B, adaptor (2680) includes an adaptor body (2682) defining a container recess (2686) and a pair of opposed guide slots (2688), a locating feature (2684), a resilient arm (2689), and a stop (2687) fixed to resilient arm (2689). As will be understood, adaptor is generally configured to be used tin insert tissue container (2500) into a drawer (2690) of a radiograph machine (2700), such that tissue container (2500) is placed in a consistent location relative to drawer (2690). Container recess (2686) is dimensioned to house tissue container (2500). Container recess (2686) may complement the underside of tissue container (2500). Guide slots (88) are dimensioned to receive at least a portion of tissue strip container (2500). Resilient arm (2689) is sufficiently resilient to deflect downwardly toward container recess (2686) in response to an external force.

Figure 14C:
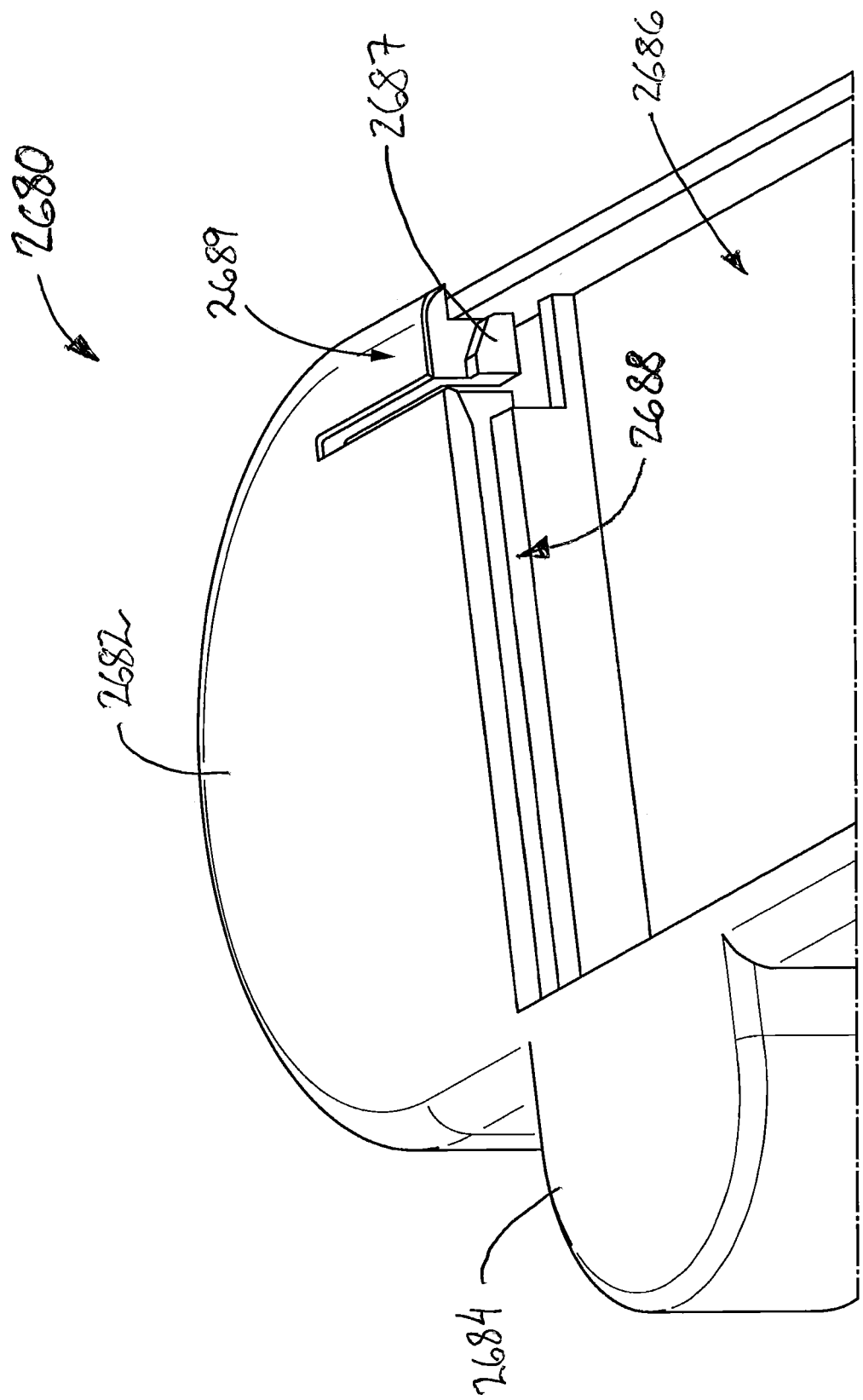
FIG. 14C depicts a detailed perspective view of the adaptor of FIG. 14B.

As best seen in FIG. 14C stop (2687) is dimensioned to abut against at least a portion of tissue container (2500) as tissue container (2500) is slid within guide slots (2688). This relationship is configured to permit deflection of resilient arm (2689) and stop (2687) downwardly toward container recess (2686). Once tissue container (2500) is sufficiently inserted into adaptor (2680), a portion of tissue container (2500) no longer contacts stop (2687), thereby allowing resilient arm (2689) and stop (2687) to return upwardly to a relaxed position. Stop (2687) is positioned to block tissue container (2500) from inadvertently exiting adaptor (2680). By way of example only, it should be understood that various features of adaptor (2680) may be configured and usable in accordance with at least some of the teachings of U.S. Ser. No. 15/638,740, entitled "Biopsy Sample Container," filed on an even date herewith, the disclosure of which is incorporated by reference herein.

Figure 14D:
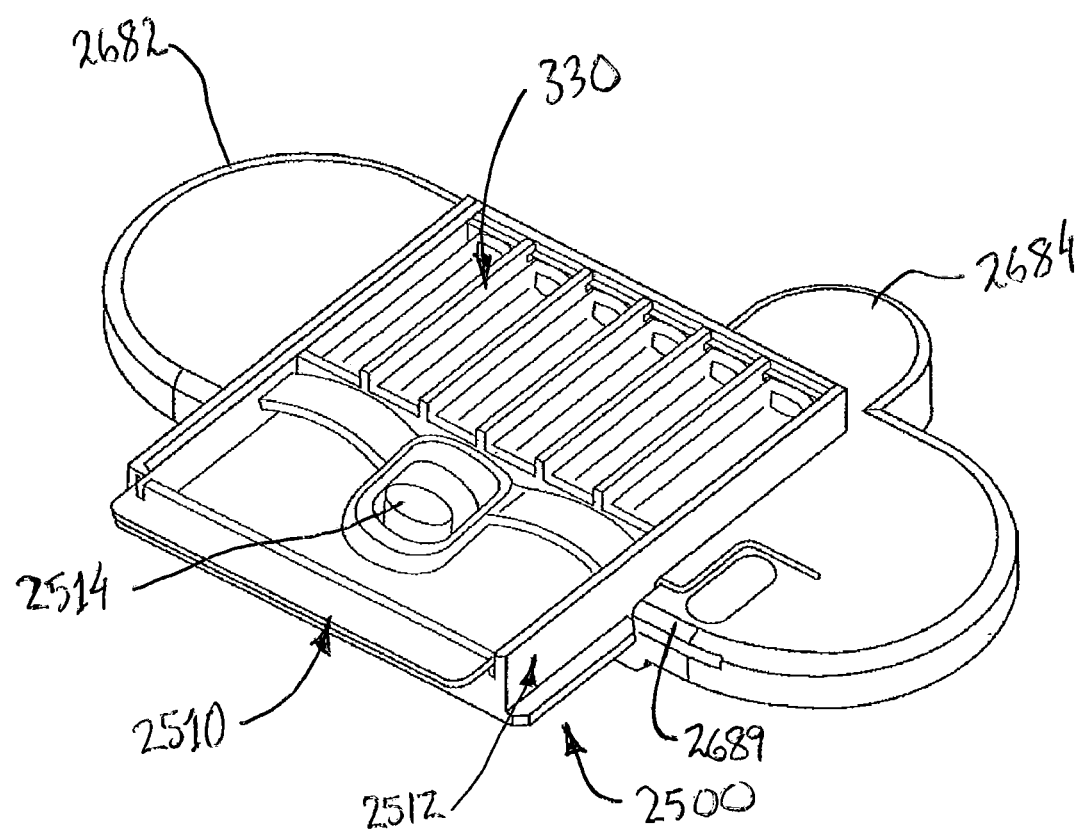
FIG. 14D depicts a perspective view of the tissue container of FIG. 13 disposed within the adaptor of FIG. 14B.

FIGS. 14B-14D show insertion of tissue container (2500) into adaptor (2680) in preparation for imaging. As can be seen, tissue container (2500) is slid laterally into adaptor (2680). This causes at least a portion of base (2512) of container (2500) to engage with slots (2688) of adaptor (2680). Once tissue container (2500) is fully inserted into adaptor (2680), stop (2687) disengages from tissue container (2500), thereby permitting resilient arm (2689) to snap upwardly and lock tissue container (2500) within adaptor (2680).

Figure 15:
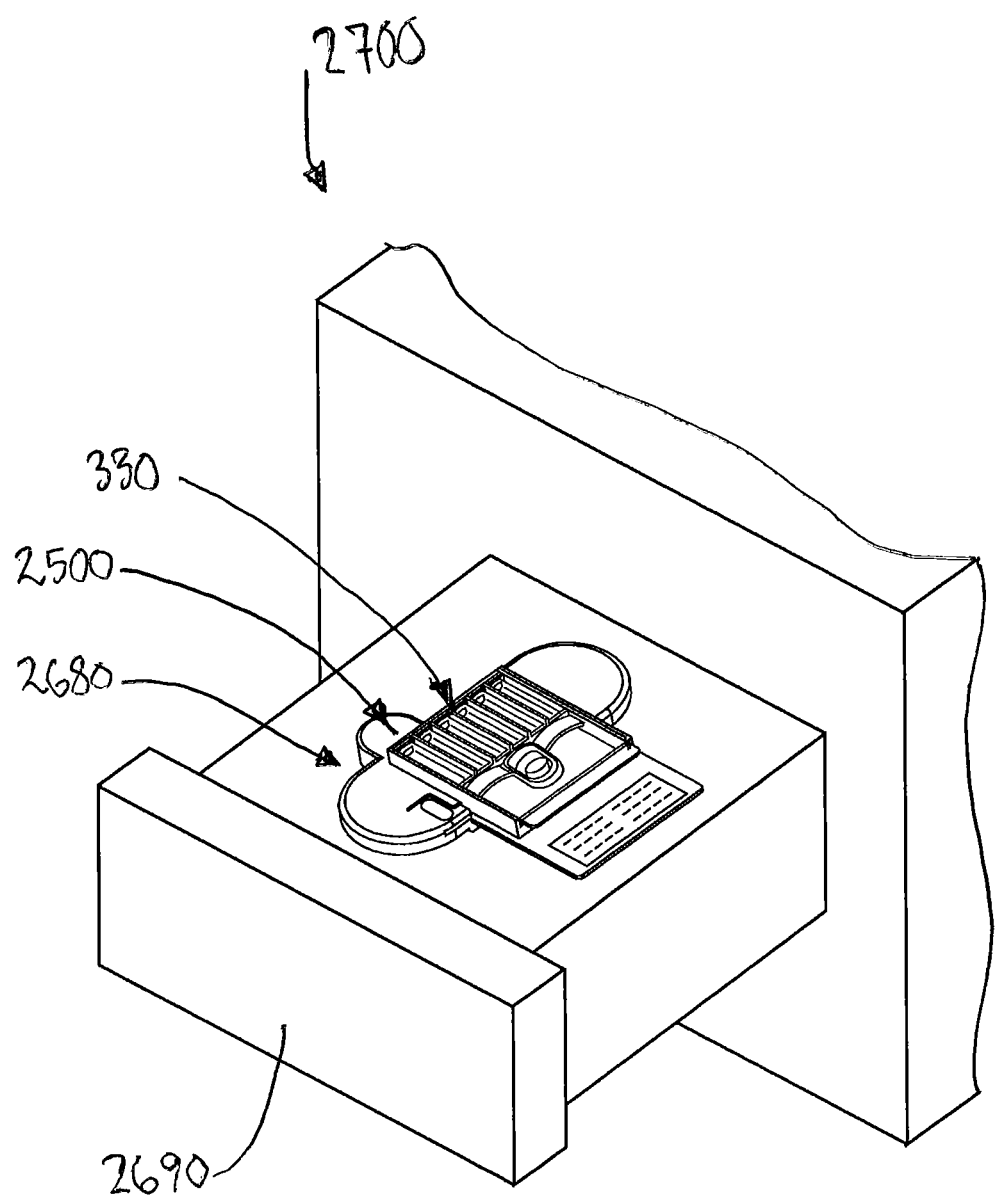
FIG. 15 depicts a perspective view of the tissue container of FIG. 13 and the adaptor of FIG. 14B being inserted into a drawer of a radiograph machine.

After tissue container (2500) is inserted into adaptor (2680), the combination of tray (330), tissue container (2500), and adaptor (2680) can be inserted into drawer (2690) of radiograph machine (2700), as shown in FIG. 15. Drawer (2690) is then closed and radiograph machine (2700) is activated to image the samples included within tray (330) using X-Ray radiation.

Figure 16:
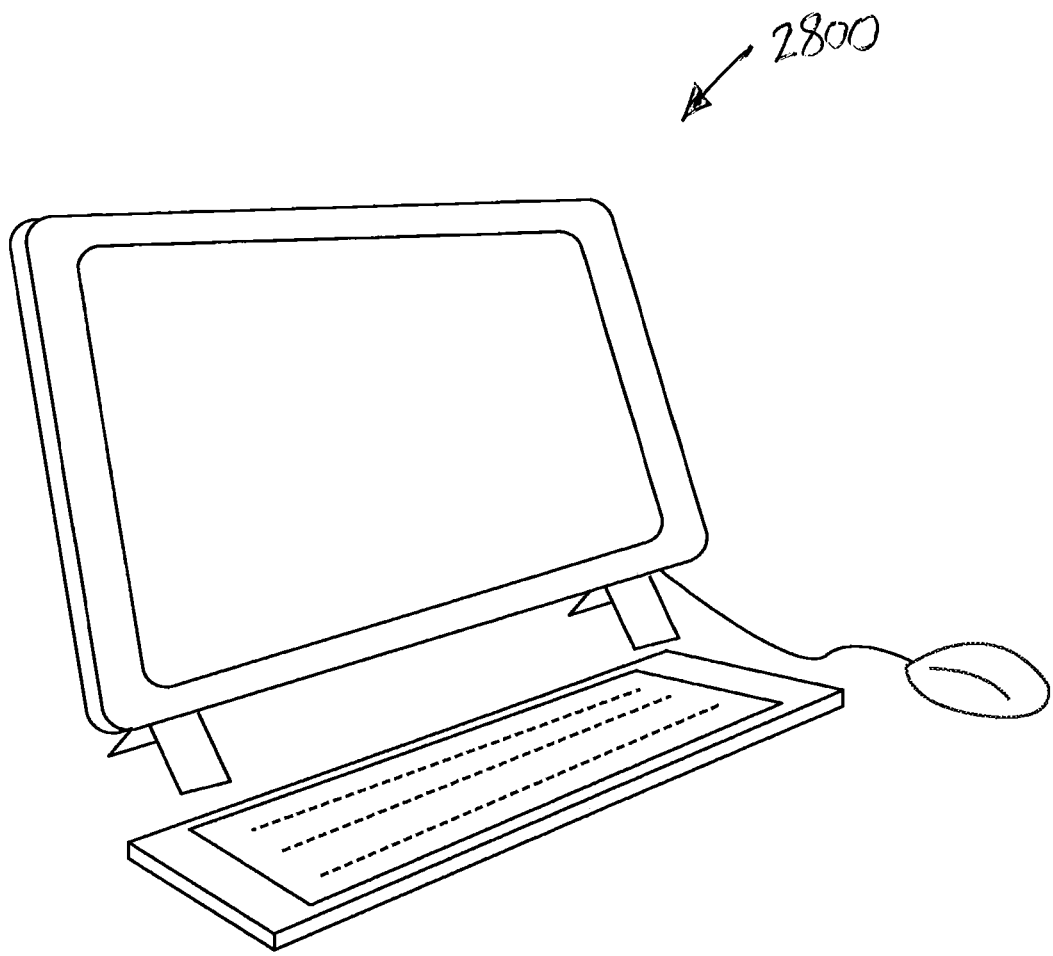
FIG. 16 depicts a perspective view of an exemplary workstation that may be used in connection with the radiograph machine of FIG. 15 for analysis of images.

After imaging, the resulting X-Ray images can be analyzed at workstation (2800) shown in FIG. 16. By way of example only, suitable analysis may include actions such as identifying calcifications or other suspicious regions that may be designated for further analysis via pathological analysis. Workstation (2800) generally comprises a commercially available computer including various components such as a display and various user input features. In some uses, workstation (2800) can also be used to record the results of the X-Ray analysis of the tissue within tray (330).

Figure 17:
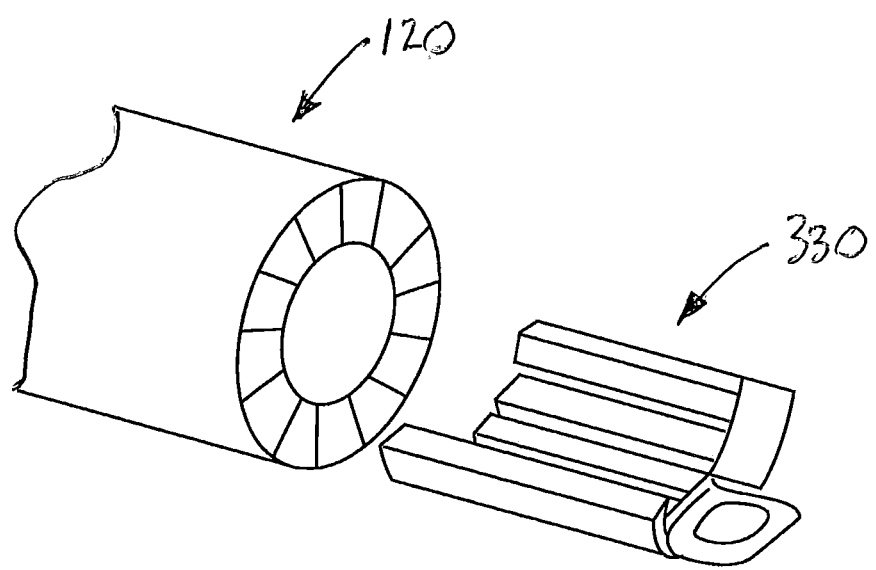
FIG. 17 depicts a perspective view of another tray being removed from a tissue sample holder of the biopsy system of FIG. 2.
Figure 18:
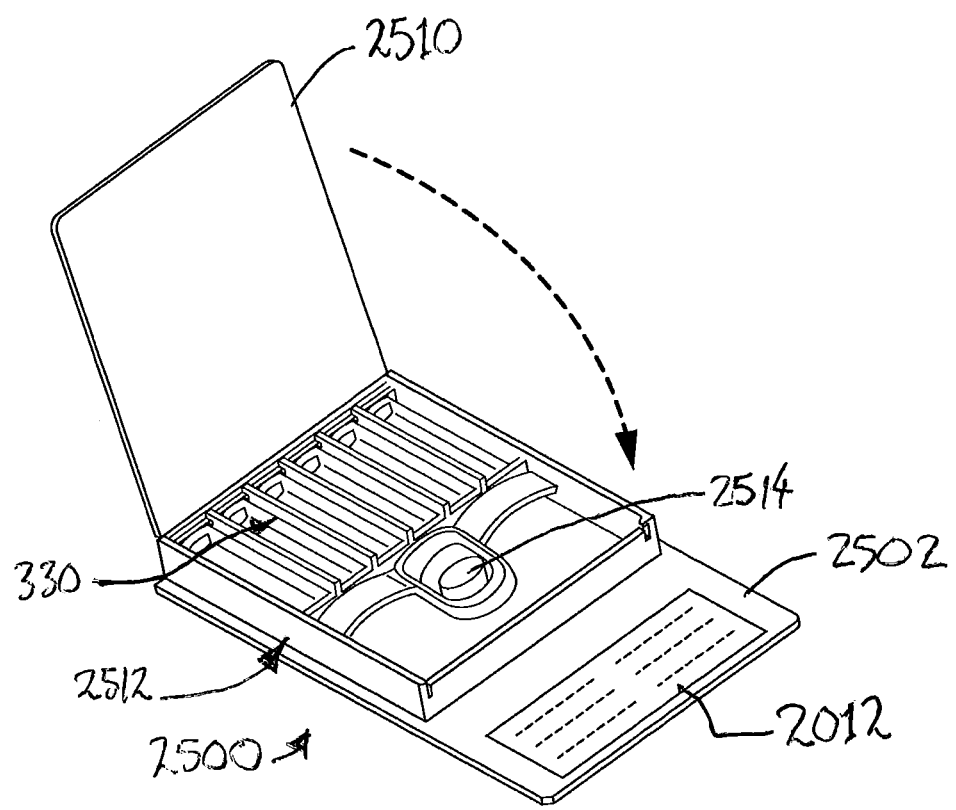
FIG. 18 depicts a perspective view of the tray of FIG. 17 inserted into another tissue container, with a lid being closed in the direction of an arrow.
Figure 19:
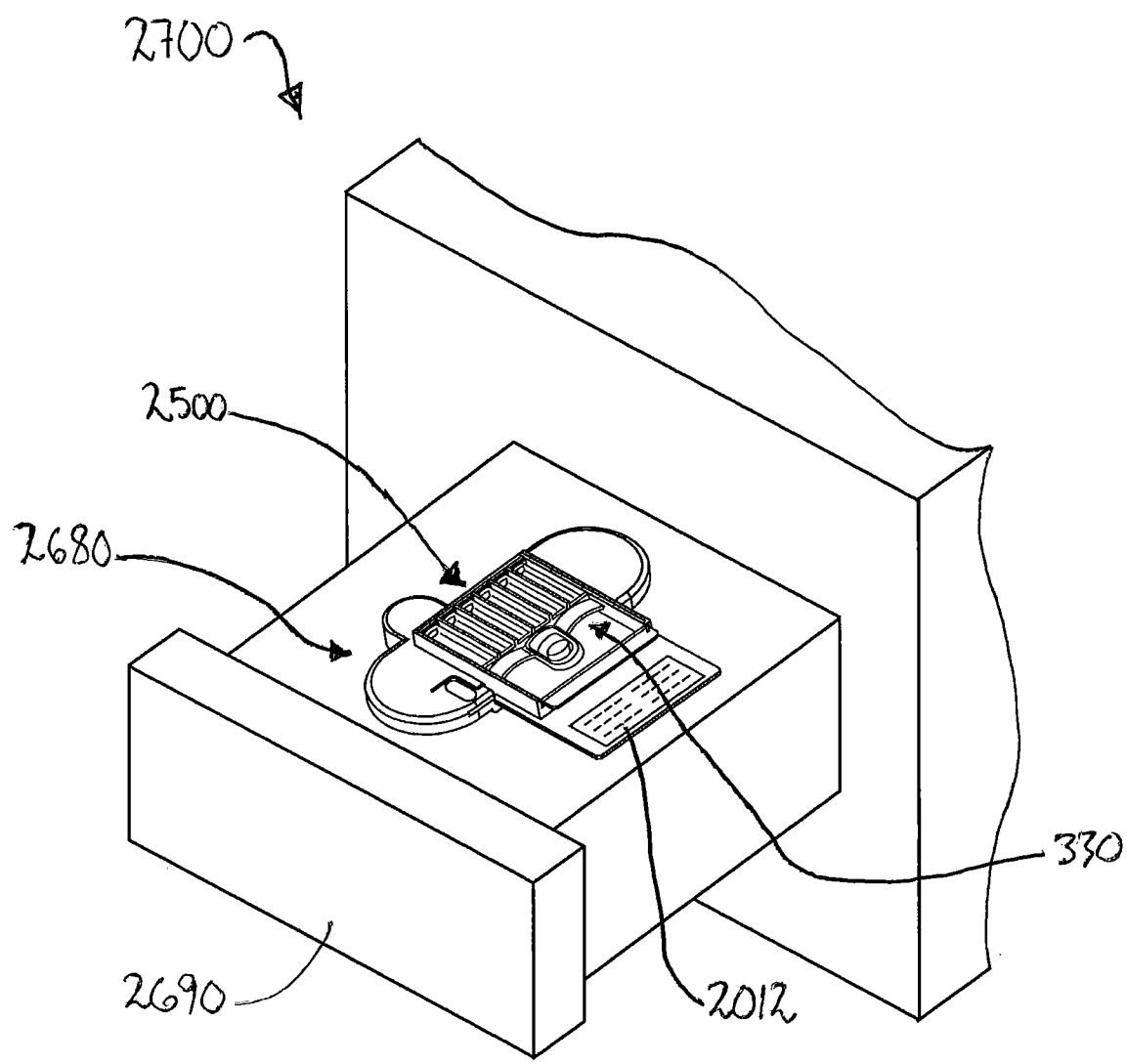
FIG. 19 depicts a perspective view of the tissue container of FIG. 18 received in an adaptor and being inserted into the drawer of the radiograph machine of FIG. 15.

FIG. 17 shows another tray (330) with another set of 6 tissue samples being removed from a portion of tissue sample holder (130) of biopsy system (102). The procedure described above with respect to FIGS. 12-16 is then repeated for the next tray (330) as shown in FIGS. 17-20. For instance, FIG. 18 shows tray (330) after it has been placed in another tissue container (2500). Cover (2510) is then closed in the direction of the arrow. Similarly, FIG. 19 shows tissue container (2500) being placed in drawer (2690) of radiograph machine (2700) after insertion of tissue container (2500) into adaptor (2680).

Figure 20:
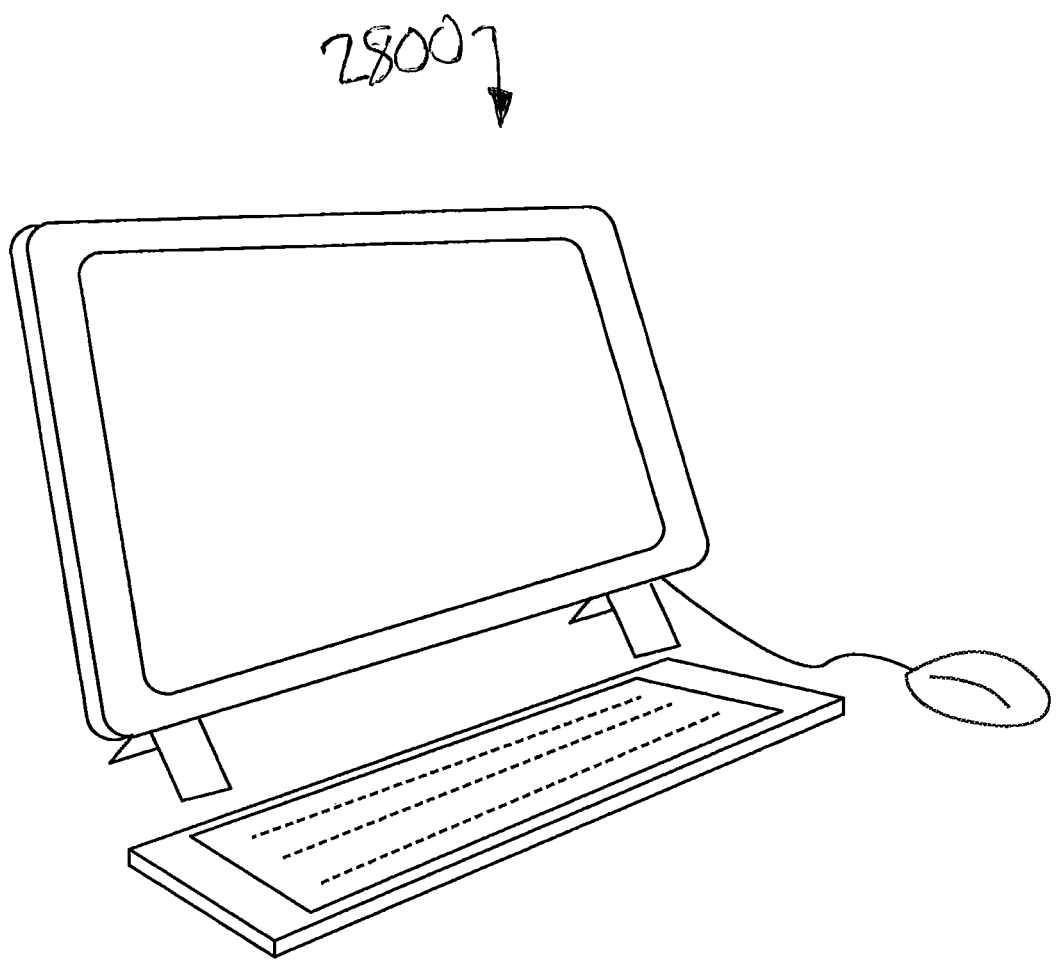
FIG. 20 depicts another perspective view of the workstation of FIG. 16.

FIG. 20 shows the computer which could be used to record the results of the X-Ray analysis of the tissue in the second tissue retainer, with the computer as being described previously in FIG. 15. Finally, FIG. 20 shows workstation (2800) being used by an operator to analyze the samples included within tray (330) after imaging via radiograph machine (2700).

Figure 21:
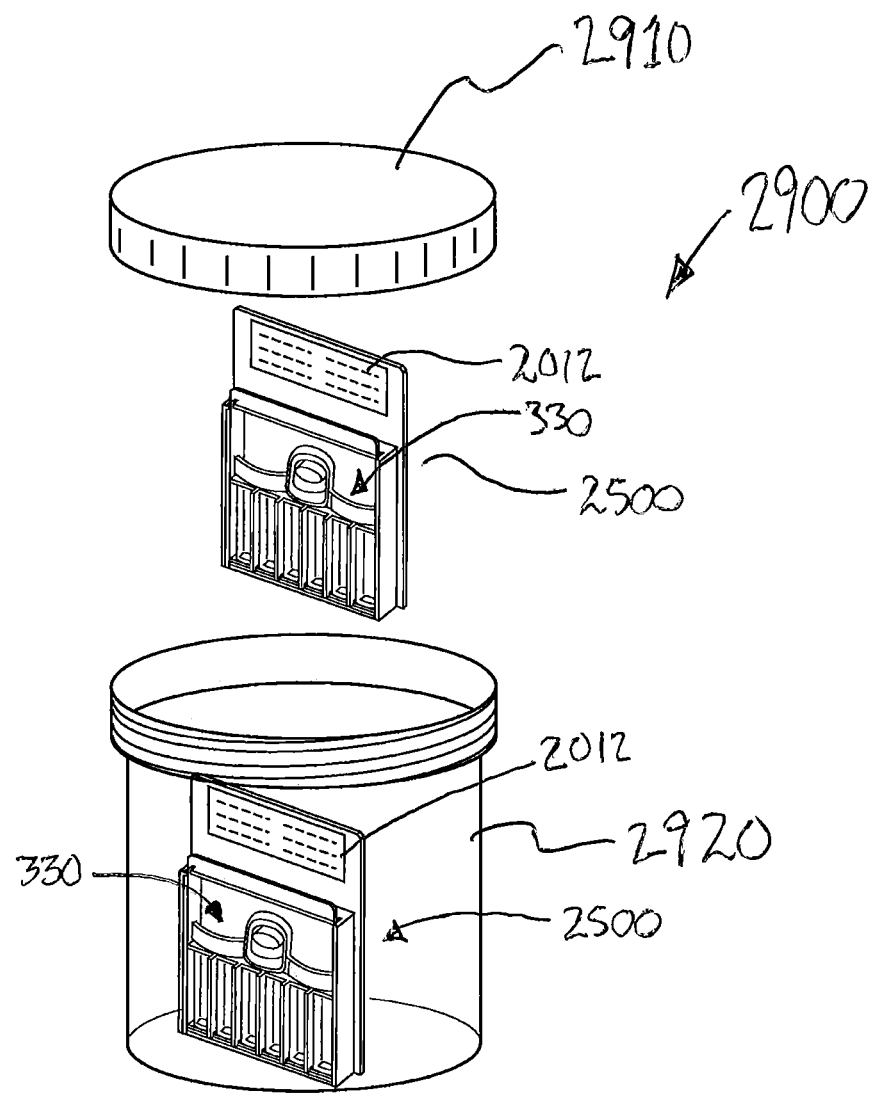
FIG. 21 depicts a perspective view of the tissue container of FIG. 13 and the tissue container of FIG. 18 disposed within a transit container, the tray of FIG. 12 and the tray of FIG. 17 disposed within each tissue container, respectively.

After tissue samples in both trays (330) have been analyzed using the imaging process described above, each tissue container (2500) can be removed from adaptor (2680). Once each tissue container (2500) is removed, FIG. 21 shows both tissue containers (2500) being inserted into a transit container (2900). Transit container (2900) of the present example includes a lid (2910) and a cup (2920). Cup (2920) is filled with a fixative such as formalin or any other suitable fluid. Once each tissue container (2500) is inserted within cup (2920) as shown in FIG. 21, the fixative may fill each tissue container (2500) to submerge each tissue sample for transit. Lid (2910) is then attached to cup (2920) such that each tissue container (2500) and accompanying tray (330) is sealed within transit container (2900) for transport.

Figure 22:
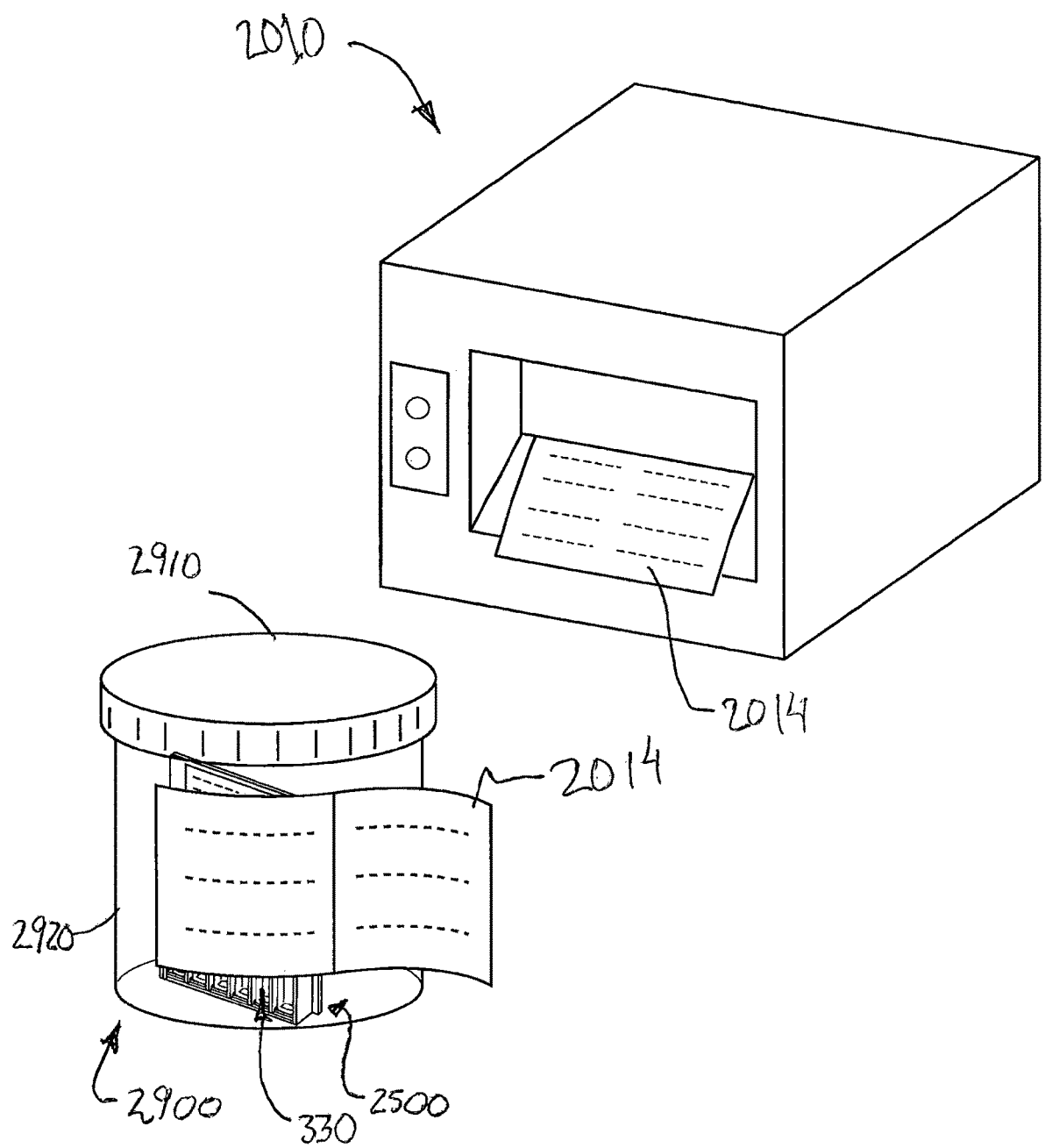
FIG. 22 depicts a perspective view of the label printer of FIG. 10 configured for printing labels for the transit container of FIG. 21.

After tissue containers (2500) and trays (330) are prepared for transit by sealing within transit container (2900), label printer (2010) can be configured to print labels (2014) for transit container (2900). As shown in FIG. 22, labels (2014) are generally configured specifically for transit container (2900). However, it should be understood that in other examples labels (2012) and labels (2014) may be configured to be substantially the same such that a common label blank may be used universally among tissue container (2500) and transit container (2900).

Figure 23:
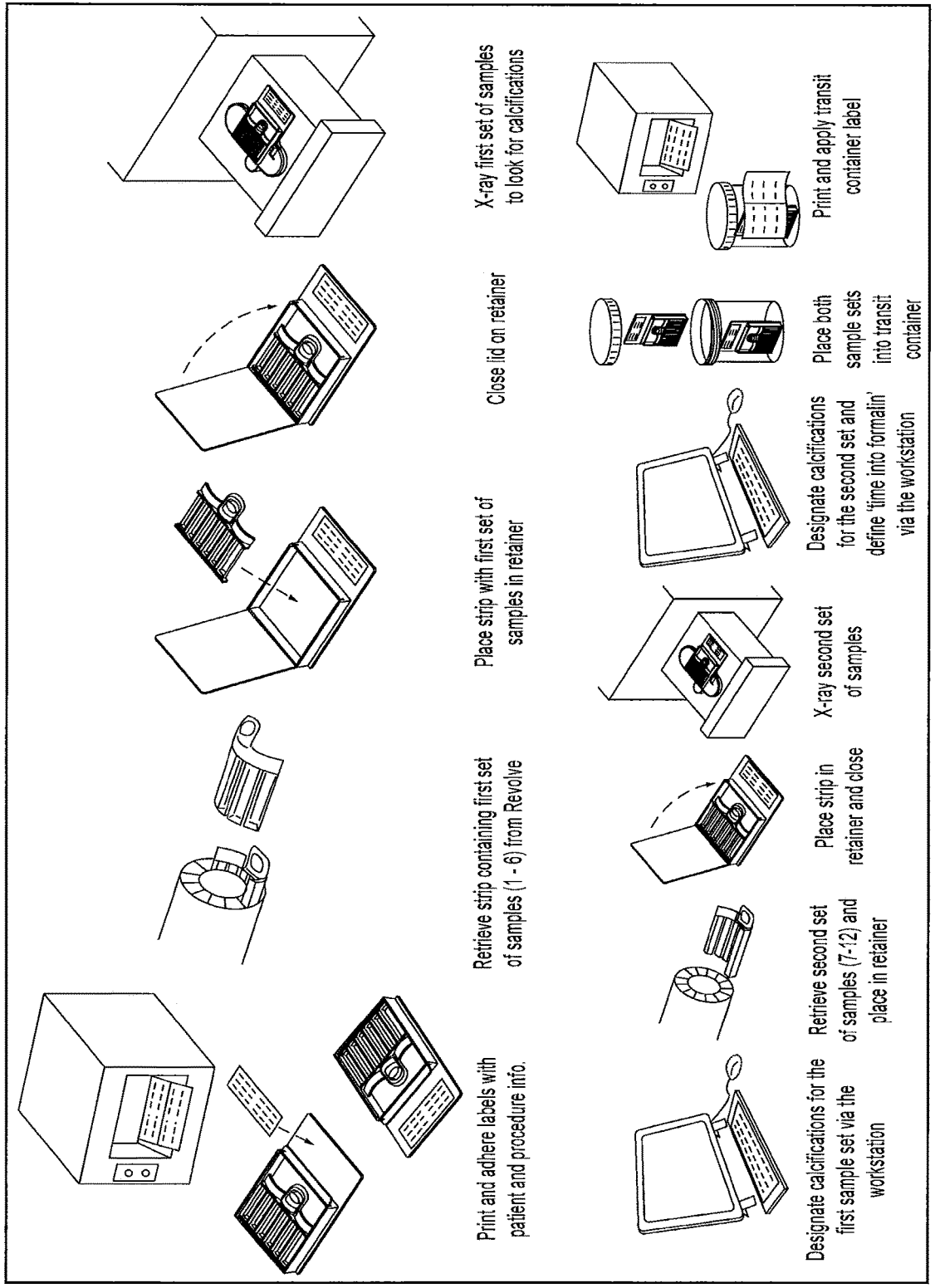
FIG. 23 depicts a composite view of the process depicted in FIGS. 10-22.

FIG. 23 shows the entire process of FIGS. 10-22, with more detail written under each drawing.

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of obtaining and analyzing at least one tissue sample utilizing a biopsy system, a tissue container, a transport container, and a tissue tracking system comprising a control unit, a printer, and a scanner, the method comprising: (a) printing a first label associated with the tissue container; (b) attaching the first label to the tissue container; (c) obtaining at least one tissue sample with the biopsy system; (d) removing the at least one tissue sample from the biopsy system; (e) placing the at least one tissue sample into the labeled tissue container; (f) printing a second label associated with the transport container; (g) attaching the second label to the transport container; and (h) scanning the first label and the second label to ensure the first label and the second label are both associated with the at least one tissue sample.

Example 2

The method of Example 1, further comprising inputting a time of removal into the control unit of the tissue tracking system, wherein the time of removal is associated with placing the at least one tissue sample into the tissue container.

Example 3

The method of any one or more of Examples 1 through 2, wherein the biopsy system further comprises a removable tissue sample tray, wherein the act of obtaining at least one tissue sample with the biopsy system comprises depositing the at least one tissue sample in the removable tissue sample tray.

Example 4

The method of Example 3, wherein placing the at least one tissue sample into the tissue container includes placing the tissue sample tray with the at least one tissue sample into the tissue container.

Example 5

The method of Example 4, wherein the tissue sample tray is flexible, wherein the act of placing the tissue sample tray into the tissue container comprises at least partially flattening the tissue sample tray in the tissue container.

Example 6

The method of any one or more of Examples 1 through 5, further comprising placing the tissue container and the first label within the transport container.

Example 7

The method of Example 6, further comprising scanning the second label after the tissue container and the first label are placed within the transport container.

Example 8

The method of Example 7, further comprising transporting the transport container containing the tissue container along with the first label and the second label to a secondary location.

Example 9

The method of Example 8, further comprising scanning the second label upon arrival to the secondary location.

Example 10

The method of Example 9, further comprising removing the tissue container from the transport container.

Example 11

The method of Example 10, further comprising scanning both the first label and the second label after removing the tissue container from the transport container to ensure the first label and the second label are associated with the at least one tissue sample.

Example 12

The method of Example 11, wherein the secondary location has a second tissue tracking system.

Example 13

The method of Example 12, wherein the first tissue tracking system comprises a first network interface, wherein the second tissue tracking system comprising a second network interface, wherein the first network interface and the second network interface are configured to communicate information with each other.

Example 14

The method of any one or more of Examples 1 through 12, further comprising a tissue imaging system, wherein the tissue container is inserted into the tissue imaging system after placing the at least one tissue sample into the tissue container.

Example 15

The method of Example 14, further comprising transporting the tissue container from a first room to a second room, where the tissue imaging system is located within the second room.

Example 16

A method of obtaining and analyzing at least one tissue sample utilizing a biopsy system, a tissue container, a first tissue tracking system comprising a first control unit, a first printer, and a first scanner, and a second tissue tracking system comprising a second control unit, a second scanner, the method comprising: (a) printing a first label associated with the tissue container; (b) attaching the first label to the tissue container; (c) obtaining at least one tissue sample with the biopsy system; (d) removing the at least one tissue sample from the biopsy system; (e) placing the at least one tissue sample into the tissue container; (f) scanning the first label with the first tissue tracking system; (g) transporting the tissue container to a secondary location, wherein the second tissue tracking system is located at the secondary location, and (h) scanning the first label with the second tissue tracking system located at the secondary location.

Example 17

The method of Example 16, further comprising: (a) labeling a transport container with a second label; and (b) placing the tissue container in the transport container before transporting the tissue container to the secondary location.

Example 18

The method of Example 17, wherein the second label is scanned by the second tissue tracking system before the first label.

Example 19

The method of Example 18, further comprising closing the tissue container, wherein the second label is printed after closing the tissue container.

Example 20

A method of obtaining and analyzing at least one tissue sample utilizing a biopsy system, a tissue container, a transport container, and a tissue tracking system comprising a control unit, a printer, and a scanner, the method comprising: (a) printing a first label associated with the tissue container; (b) attaching the first label to the tissue container; (c) obtaining at least one tissue sample with the biopsy system; (d) removing the at least one tissue sample from the biopsy system; (e) placing the at least one tissue sample into the tissue container; (f) printing a second label associated with the transport container; (g) attaching the second label to the transport container; (h) scanning the first label and the second label to ensure the first label and the second label are both associated with the at least one tissue sample; (i) placing the tissue container within the transport container; (j) scanning the transport container; (k) transporting the tissue container within the transport container to a secondary location; and (l) scanning the transport container after reaching the secondary location.

Example 21

A method of obtaining and analyzing at least one tissue sample utilizing a biopsy system, a tissue container, a transport container, and a tissue tracking system comprising a control unit, a printer, and a scanner, the method comprising: (a) printing a first label associated with the tissue container; (b) attaching the first label to the tissue container; (c) obtaining at least one tissue sample with the biopsy system; (d) removing the at least one tissue sample from the biopsy system; (e) placing the at least one tissue sample into the labeled tissue container; (f) scanning the labeled tissue container; (g) printing a second label, based on the scanned information, associated with the transport container; and (h) attaching the second label to the transport container.

Example 22

A method of obtaining and analyzing at least one tissue sample utilizing a biopsy system, a tissue container, a formalin jar, and a tissue tracking system comprising a control unit, a printer, and a scanner, the method comprising: (a) printing a first label associated with the tissue container; (b) attaching the first label to the tissue container; (c) obtaining at least one tissue sample with the biopsy system; (d) removing the at least one tissue sample from the biopsy system; (e) placing the at least one tissue sample into the labeled tissue container; (f) placing the labeled tissue container in an imaging apparatus (X-ray).

IX. Miscellaneous

Having shown and described various embodiments of the present invention, further adaptations of the methods and systems described herein may be accomplished by appropriate modifications by one of ordinary skill in the art without departing from the scope of the present invention.

Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A method of processing at least one tissue sample which has been removed from a patient using a biopsy system, the method comprising:
    (a) depositing the at least one tissue sample into a flexible tissue sample tray by transporting the at least one tissue sample though a hollow cutter of the biopsy system and into the flexible tissue sample tray;
    (b) removing the at least one tissue sample from the biopsy system, the act of removing the at least one tissue sample from the biopsy system including removing the flexible tissue sample tray away from the biopsy system;
    (c) forming, in a tissue container, first tracking data associated with the at least one tissue sample;
    (d) forming, in a transport container, second tracking data including one or more elements of the first tracking data and associated with the at least one tissue sample;
    (e) placing the tissue container containing the at least one tissue sample into the transport container at a first location associated with removal of the at least one tissue sample, the flexible tissue sample tray corresponding to a shape of the tissue container once placed in the tissue container;
    (f) scanning the first tracking data and the second tracking data from the tissue container and the transport container at the first location with an electronic scanning system to ensure that the first tracking data and the second tracking data are both associated with the at least one tissue sample at the point of removing the at least one tissue sample;
    (g) transporting the transport container containing the tissue container to a second location after formation of the first tracking data and the second tracking data;
    (h) scanning the second tracking data upon arrival to the second location; and
    (i) confirming, using one or more control units, an at least partially matching relationship between the first tracking data and the second tracking data after scanning the second tracking data.

2. The method of claim 1, the scanning of the first tracking data and the second tracking data is performed at the same location as where the biopsy is performed.

3. The method of claim 1, further comprising inputting a time of removal into a control unit of the one or more control units, the time of removal being associated with placing the at least one tissue sample into the tissue container.

4. The method of claim 1, placing the at least one tissue sample into the tissue container including placing the tissue sample tray with the at least one tissue sample into the tissue container, the act of placing the tissue sample tray into the tissue container including at least partially flattening the tissue sample tray in the tissue container.

5. The method of claim 1, further comprising placing the tissue container within the transport container after forming the first tracking data, and further comprising forming the second tracking data after the tissue container is placed within the transport container.

6. The method of claim 1, further comprising removing the tissue container from the transport container and scanning both the first tracking data and the second tracking data after removing the tissue container from the transport container to ensure the first tracking data and the second tracking data are associated with the at least one tissue sample.

7. The method of claim 6, the location where the biopsy being performed having a first tissue tracking system, the second location having a second tissue tracking system.

8. The method of claim 7, the first tissue tracking system including a first network interface, the second tissue tracking system including a second network interface, the first network interface and the second network interface being configured to communicate information with each other.

9. The method of claim 1, further comprising transmitting the first tracking data and the second tracking data to a laboratory information system for access by a laboratory worker for purposes of ensuring that the transmitted data match the first tracking data and the second tracking data scanned from the actual transport container and the tissue container.

10. The method of claim 1, the steps of forming the first tracking data and the second tracking data including programming the first tracking data and the second tracking data into RF ID chips disposed within the transport container and the tissue container, respectively.

11. The method of claim 1, the steps of forming the first tracking data and the second tracking data including printing a first bar label and a second bar label, and placing each bar label on the tissue container and the transport container, respectively.

12. A method of obtaining and processing at least one tissue sample utilizing a biopsy system including a needle and a cutter disposed within the needle, the method comprising:
   (a) forming a first data unit;
   (b) associating the first data unit with a tissue container;
   (c) obtaining the at least one tissue sample by moving the cutter of the biopsy system relative to the needle of the biopsy system and transporting the at least one tissue sample through the cutter and into a tissue sample tray, the tissue sample tray being disposed within a portion of the biopsy system;
   (d) placing at least one tissue sample into the tissue container at a first location by removing the tissue sample tray containing the at least one tissue sample from the biopsy system and placing the tissue sample tray into the tissue container, the act of placing the tissue sample tray into the tissue container including flexing at least a portion of the tissue sample tray to correspond to a shape of the tissue container;
   (e) scanning the first data unit with a first tissue tracking system at the first location to associate the first data unit with the at least one tissue sample obtained at the first location;
   (f) transporting the tissue container to a second location, separated from the first location, a second tissue tracking system being located at the second location,
   (g) scanning the first data unit with the second tissue tracking system located at the second location; and
   (h) confirming that scanning of the first data unit at the second location matches scanning at the first location using the second tissue tracking system.

13. The method of claim 12, further comprising:
   (a) associating a transport container with a second data unit; and
   (b) placing the tissue container in the transport container before transporting the tissue container to the second location.

14. The method of claim 13, the second data unit being scanned by the second tissue tracking system before the first data unit.

15. The method of claim 14, further comprising closing the tissue container, the second data unit being printed after closing the tissue container.

16. A method of obtaining and processing at least one tissue sample utilizing a biopsy system, the biopsy system including a cutter and a needle configured for collecting the at least one tissue sample, the biopsy system being associated with a tissue sample tray removably received within the biopsy system and configured for collection of the at least one tissue sample, the method comprising:
   (a) printing a first label associated with a tissue container;
   (b) attaching the first label to the tissue container;
   (c) removing the tissue sample tray containing the at least one tissue sample from the biopsy system;
   (d) placing the tissue sample tray containing the at least one tissue sample into the tissue container, the act of placing the tissue sample tray into the tissue container including flattening a portion of the tissue sample tray such that the tissue sample tray corresponds to a shape of the tissue container;
   (e) printing a second label associated with a transport container;
   (f) attaching the second label to the transport container;
   (g) scanning the first label and the second label at a primary location associated with obtaining the at least one tissue sample to ensure the first label and the second label are both associated with the at least one tissue sample;
   (h) placing the tissue container within the transport container;
   (i) scanning the transport container to associate the transport container with the tissue container;
   (j) receiving the tissue container within the transport container at a secondary location; and
   (k) scanning the transport container and the tissue container after reaching the secondary location; and
   (l) confirming scanning at the secondary location at least partially matches scanning performed at the primary location with a control unit.

* * * * *